US011111303B2

(12) United States Patent
Mathew et al.

(10) Patent No.: US 11,111,303 B2
(45) Date of Patent: Sep. 7, 2021

(54) COMPOSITIONS AND METHODS FOR ACTIVATION OF NK CELLS KILLING OF PROSTATE CANCER AND BREAST CANCER CELLS

(71) Applicant: UNIVERSITY OF NORTH TEXAS HEALTH SCIENCE CENTER, Ft. Worth, TX (US)

(72) Inventors: Purunelloor A. Mathew, Ft. Worth, TX (US); Stephen O. Mathew, Ft. Worth, TX (US)

(73) Assignee: UNIVERSITY OF NORTH TEXAS HEALTH SCIENCE CENTER, Ft. Worth, TX (US)

( * ) Notice: Subject to any disclaimer, the term of this patent is extended or adjusted under 35 U.S.C. 154(b) by 265 days.

(21) Appl. No.: 16/125,091

(22) Filed: Sep. 7, 2018

(65) Prior Publication Data

US 2019/0071505 A1 Mar. 7, 2019

Related U.S. Application Data

(60) Provisional application No. 62/555,566, filed on Sep. 7, 2017.

(51) Int. Cl.
| | |
|---|---|
| *C07K 16/28* | (2006.01) |
| *A61K 47/68* | (2017.01) |
| *A61K 9/00* | (2006.01) |
| *A61K 51/10* | (2006.01) |
| *A61P 35/00* | (2006.01) |
| *A61K 39/00* | (2006.01) |

(52) U.S. Cl.
CPC ........ *C07K 16/2851* (2013.01); *A61K 9/0019* (2013.01); *A61K 47/6803* (2017.08); *A61K 47/6809* (2017.08); *A61K 47/6849* (2017.08); *A61K 51/1027* (2013.01); *A61P 35/00* (2018.01); *A61K 2039/54* (2013.01); *A61K 2039/572* (2013.01); *C07K 2317/20* (2013.01); *C07K 2317/21* (2013.01); *C07K 2317/24* (2013.01); *C07K 2317/565* (2013.01); *C07K 2317/622* (2013.01); *C07K 2317/73* (2013.01); *C07K 2317/732* (2013.01); *C07K 2317/734* (2013.01); *C07K 2317/76* (2013.01)

(58) Field of Classification Search
CPC ............ A61K 47/6803; A61K 47/6809; A61K 51/1027; A61K 47/6849; C07K 16/2851
See application file for complete search history.

(56) References Cited

U.S. PATENT DOCUMENTS

2006/0002892 A1* 1/2006 Mathew .............. A61K 38/178
424/85.6

FOREIGN PATENT DOCUMENTS

WO WO-2012000994 A1 * 1/2012 ......... G01N 33/6872

OTHER PUBLICATIONS

Holliger, P. et al. Engineered antibody fragments and the rise of single domains, Nature Biotech. 2005, 23 (9): 1126-1136, Published on Sep. 7, 2005 (Year: 2005).*
Bird, et al., "Single-Chain Antigen-Binding Proteins," *Science*, 242; 423-426, 1988.
Boerner, et al., "Production of Antigen-Specific Human Monoclonal Antibodies from In Vitro-Primed Human Splenocytes," *Journal of Immunology*, 147(1); 86-95, 1991.
Butler, et al., "The Amplified ELSIA: Principles of and Applications for the Comparative Quantitation of Class and Subclass Antibodies and the Distribution of Antibodies and Atigens in Biochemical Separates," *Methods in Enzymology*, 73(Pt B); 482-523, 1981.
Colcher, et al., "Use of Monoclonal Antibodes to Define the Diversity of Mammary Tumor Viral Gene Products in Virions and Mammary Tumors of the Genus *Mus*," *Cancer Research*, 41: 1451-1459, 1981.
Cole, et al., "Monoclonal Antibodies and Cancer Therapy," *Journal of Cellular Biochemistry*, vol. 29, No. 59A, 1985, pp. 33-74. Doi: 10.1002/jcb.240290503, Abstract.
Holliger, et al., "Diabodies: Small Bivalent and Bispecific Antibody Fragments," *PNAS*, 444-6448, 1993.
Hoogenboom & Winter, "By-Passing Immunisation. Human Antibodies from Synthetic Repertoires of Germline VH Gene Segments Rearranged In Vitro," *Journal of Molecular Biology*, 227(2); 381-388, 1992.
Huston, et al., "Protein Engineering of Antibody Binding Sites: Recovery of Specific Activity in an Anti-Digoxin Single-Chain Fv Analogue Produced in *Escherichia coli*," *PNAS*, 85(16); 5879-5883, 1988.
Jakobovits, et al., "Germ-Line Transmission and Expression of a Human-Derived Yeast Artificial Chromosome," *Nature*, 362; 255-258, 1993.
Jakobovits, et al., "Analysis of Homozygous Mutant Chimeric Mice: Deletion of the Immunoglobulin Heavy-Chain Joining Region Blocks B-Cell Development and Antibody Production," *PNAS*, 90(6); 2551-2555, 1993.
Kohler & Milstein, "Continuous Cultures of Fused Cells Secreting Antibody of Predefined Specificity," *Nature*, 256; 495-497, 1975.
Kostelny, et al., "Formation of Bispecific Antibody by the Use of Leucine Zippers," *Journal of Immunology*, 148(5); 1547-1553, 1992.
Marks, et al., "By-Passing Immunization Human Antibodies from V-Gene Libraries Displayed on Phage," *Journal of Molecular Biology*, 222(3); 581-597.

(Continued)

*Primary Examiner* — Peter J Reddig
*Assistant Examiner* — Cheng Lu
(74) *Attorney, Agent, or Firm* — Norton Rose Fulbright US LLP

(57) ABSTRACT

Certain embodiments are directed to methods of treating LLT1 expressing cancer by administering to a subject having an LLT1 expressing cancer an LLT1 inhibitor.

22 Claims, 16 Drawing Sheets
(4 of 16 Drawing Sheet(s) Filed in Color)
Specification includes a Sequence Listing.

(56) References Cited

OTHER PUBLICATIONS

Mathew, et al., "Overexpression of LLT1 (OCIL, CLEC2D) on Prostate Cancer Cells Inhibits NK Cell-Mediated Killing Through LLT1-NKRP1A (CD161) Interaction," Oncotarget, Advance Publications, 2016.

Needleman & Wunsch, "A General Method Applicable to the Search for Similarities in the Amino Acid Sequence of Two Proteins," *Journal of Molecular Biology*, 48(3), 443-453, 1970.

Pearson & Lipman, "Improved Tools for Biological Sequence Comparison," *PNAS*, 85; 2444-2448, 1988.

Poljak, et al., "Production and Structure of Diabodies," Structure, 2; 1121-1123, 1994.

Smith & Waterman, "Comparison of Biosequences," *Advances in Applied Mathematics*, 2(4), 482-489, 1981.

Songsivilai & Lachmann, "Bispecific Antibody: A Tool for Diagnosis and Treatment of Disease," *Clinical & Experimental Immunology*, 79(3); 315-321, 1990.

Spieker-Polet, "Rabbit Monoclonal Antibodies: Generating a Fusion Partner to Produce Rabbit-Rabbit Hybridomas," *PNAS*, 92; 9348-9352.

Strejan, et al., "Suppression of Chronic-Relapsing Experimental Allergic Encephalomyelitis in Strain-13 Guinea Pigs by Administration of Liposome-Associated Myelin Basic Protein," *Journal of Neuroimmunology*, 7; 27-41, 1984-1985.

Van Dijk & Van de Winkel, "Human Antibodies as Next Generation Therapeutics," *Current Opinion in Chemical Biology*, 5(4); 368-374, 2001.

Voller, et al., "Enzyme Immunoassays with Special Reference to ELISA Techniques," *Journal of Clinical Pathology*, 31(6); 507-520, 1978.

Ward, et al., "Binding Activities of a Repertoire of Single Immunoglobulin Variable Domains Secreted from *Escherichia coli*," *Nature*, 341(6242); 544-346, 1989.

\* cited by examiner

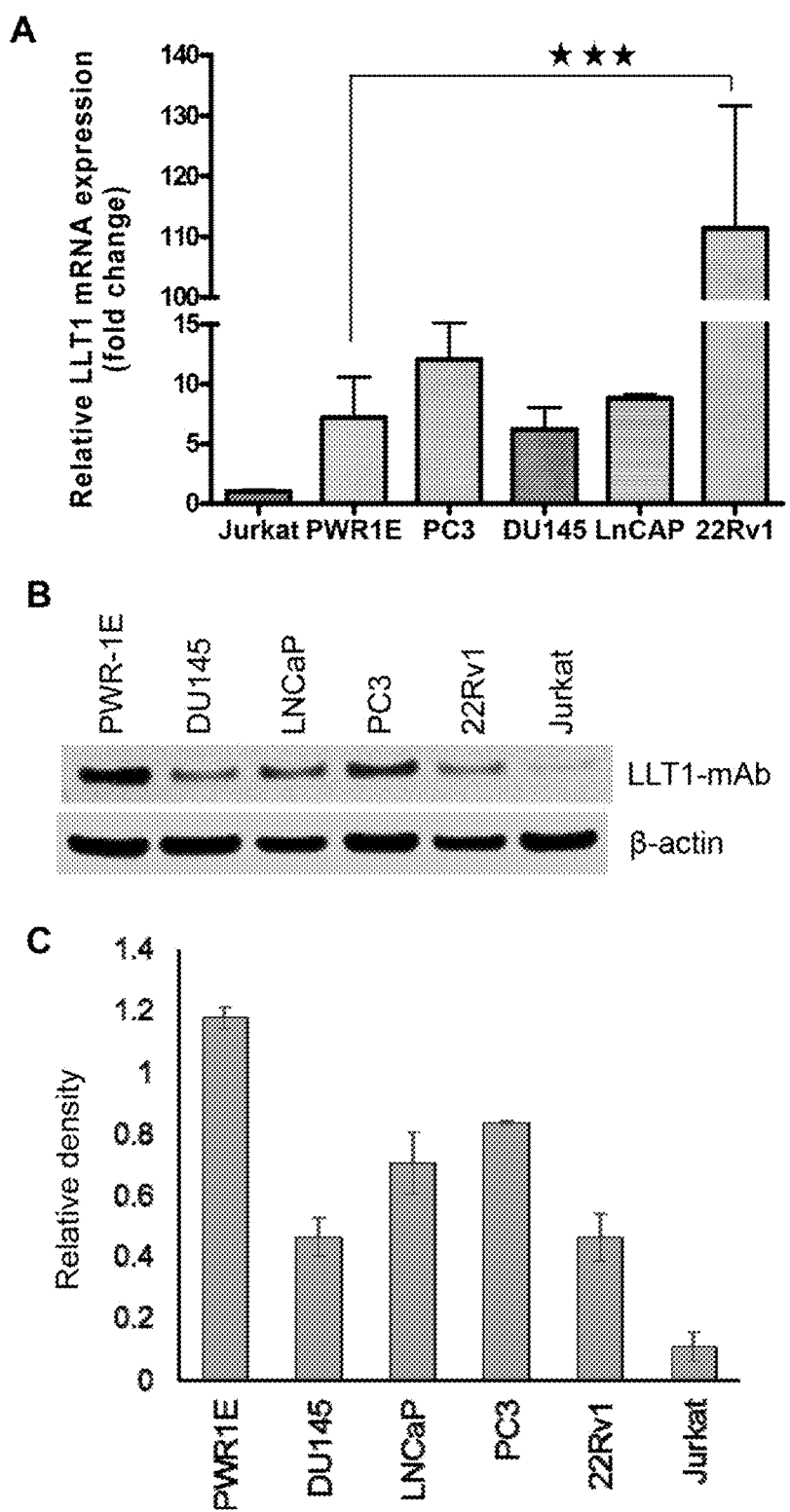
FIGS. 1A-C

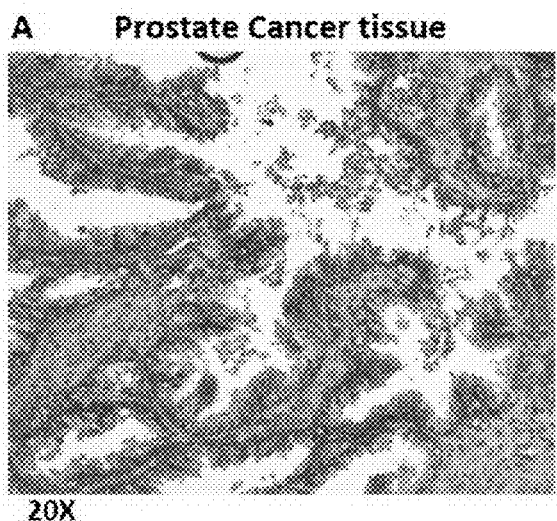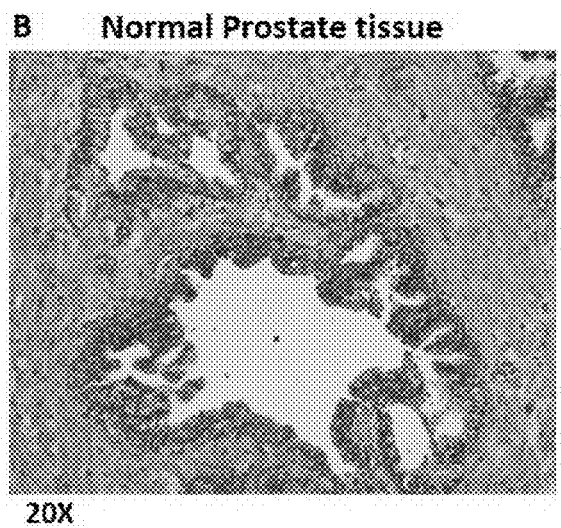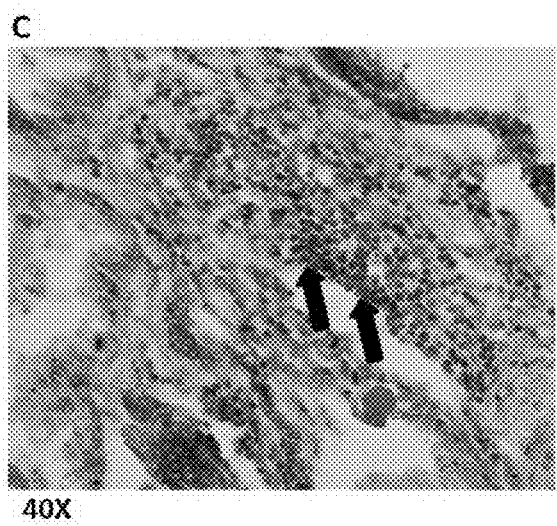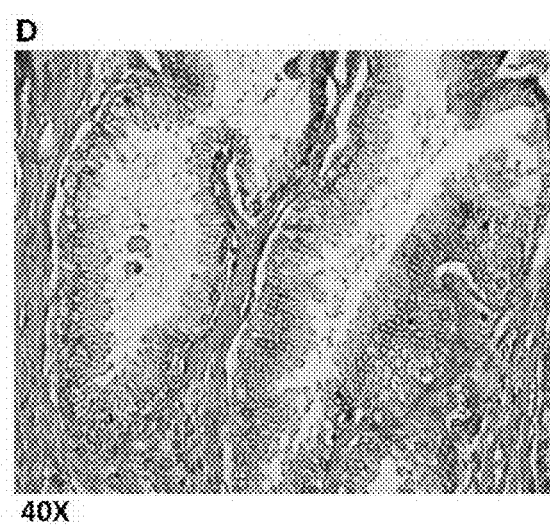
FIGS. 4A-D

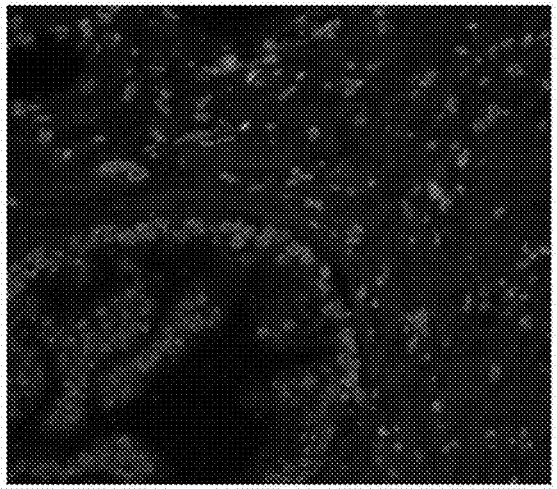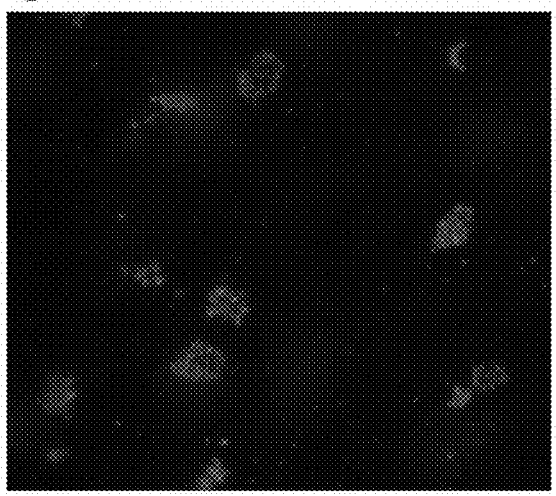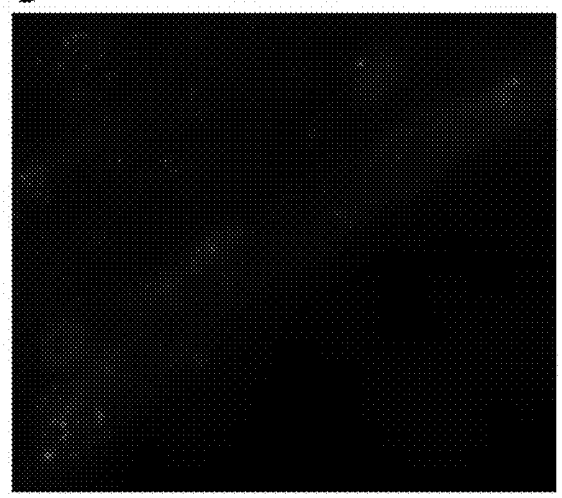
FIGS. 5A-D

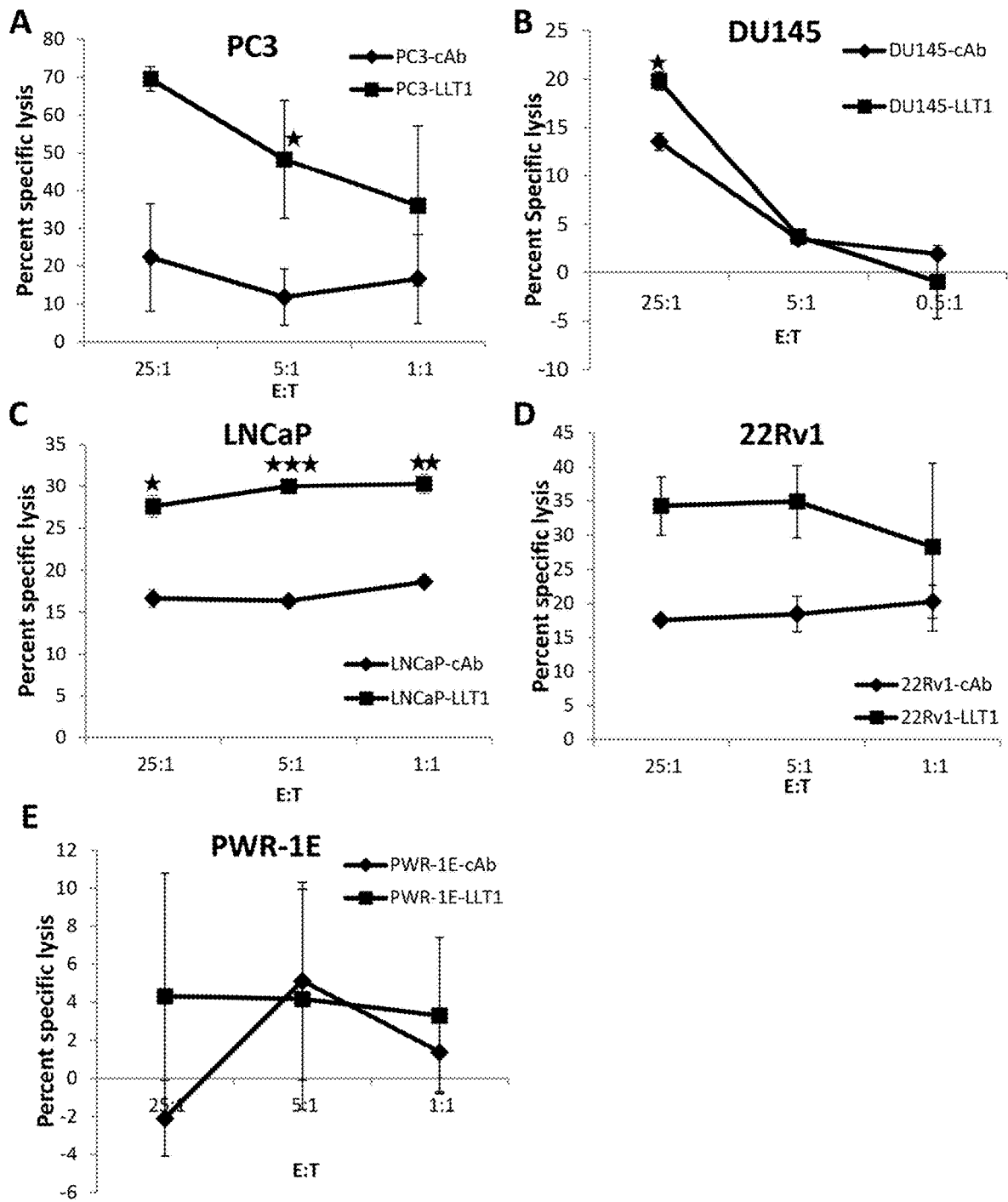
FIGS. 6A-E

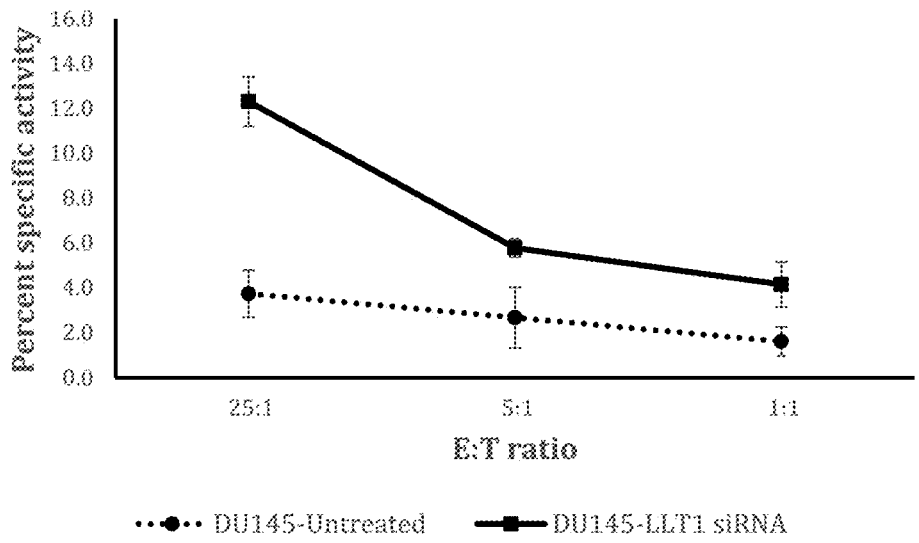
FIG. 9
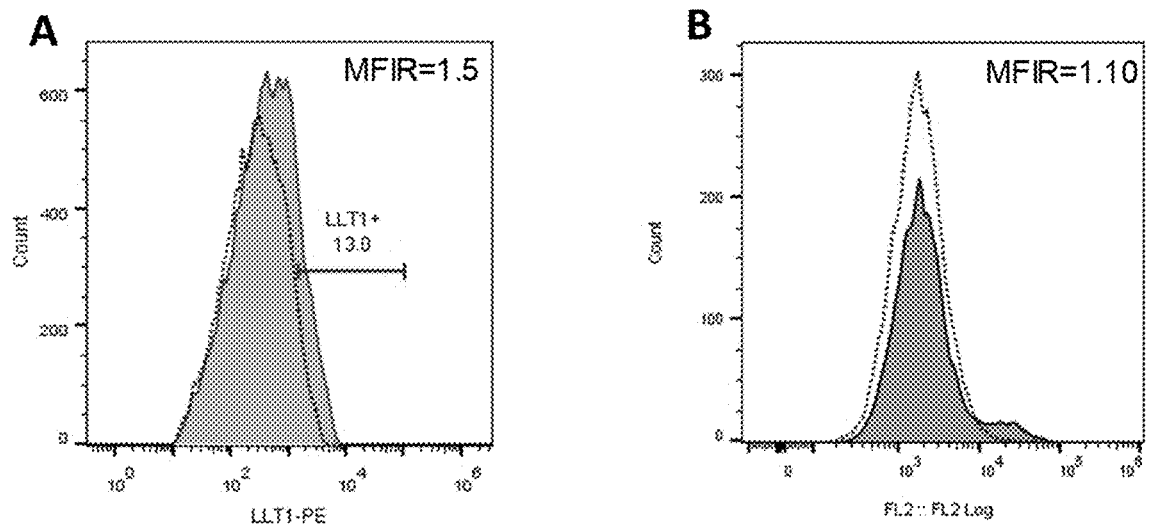
FIGS. 10A-B

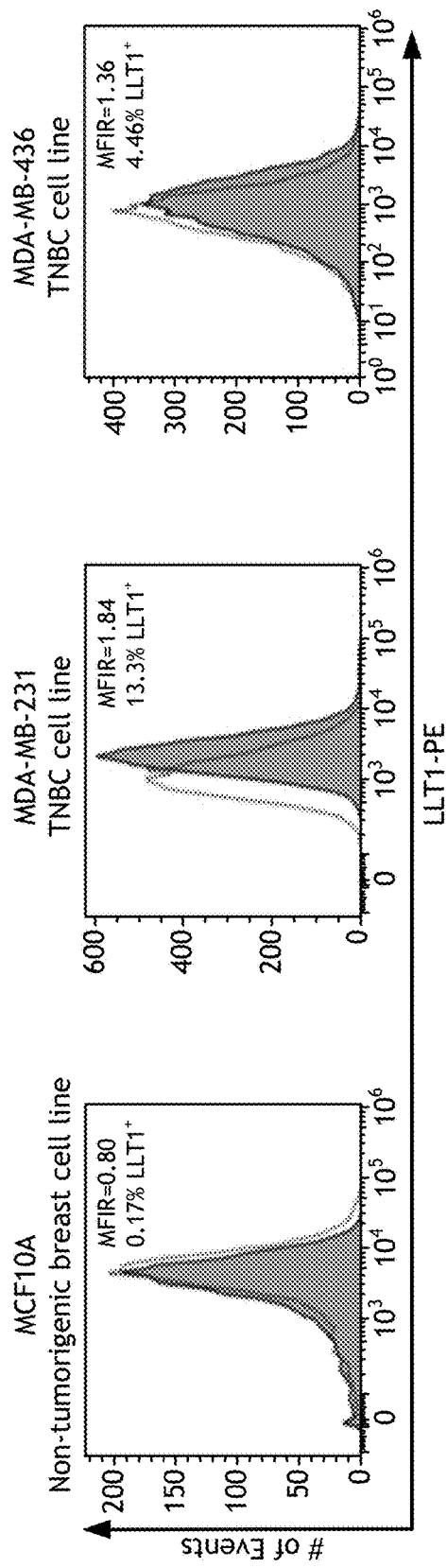
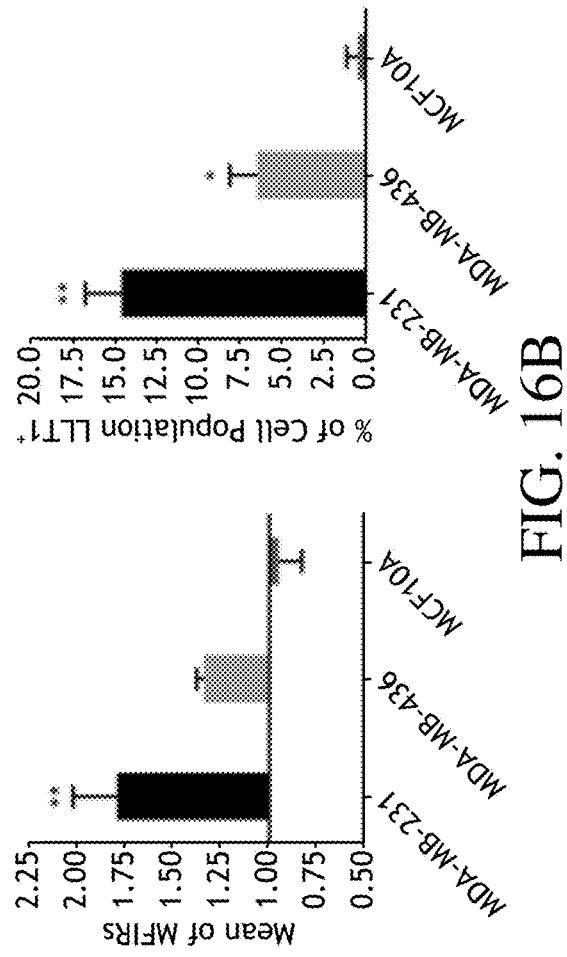
FIG. 16A
FIG. 16B

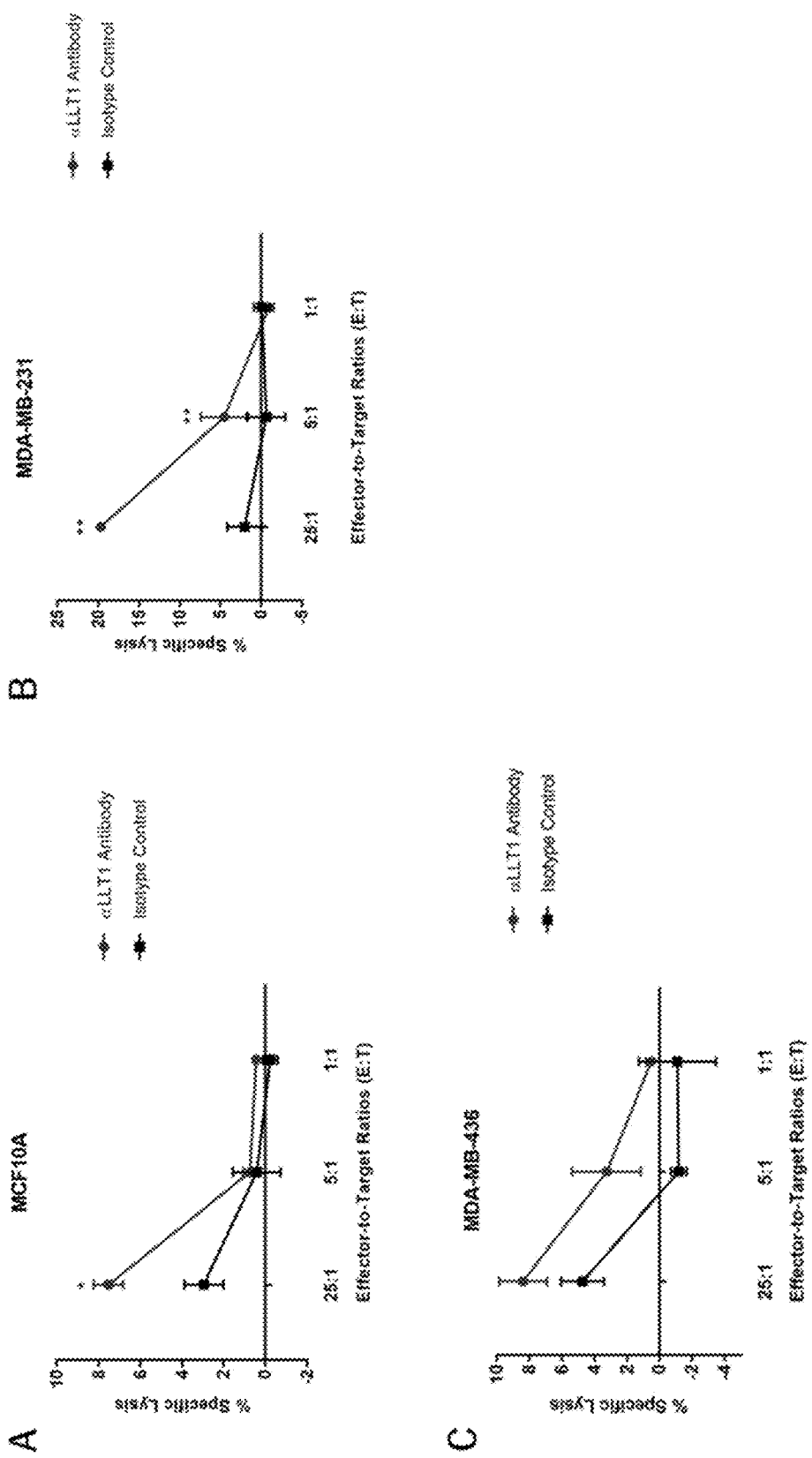
FIGS. 19A-C

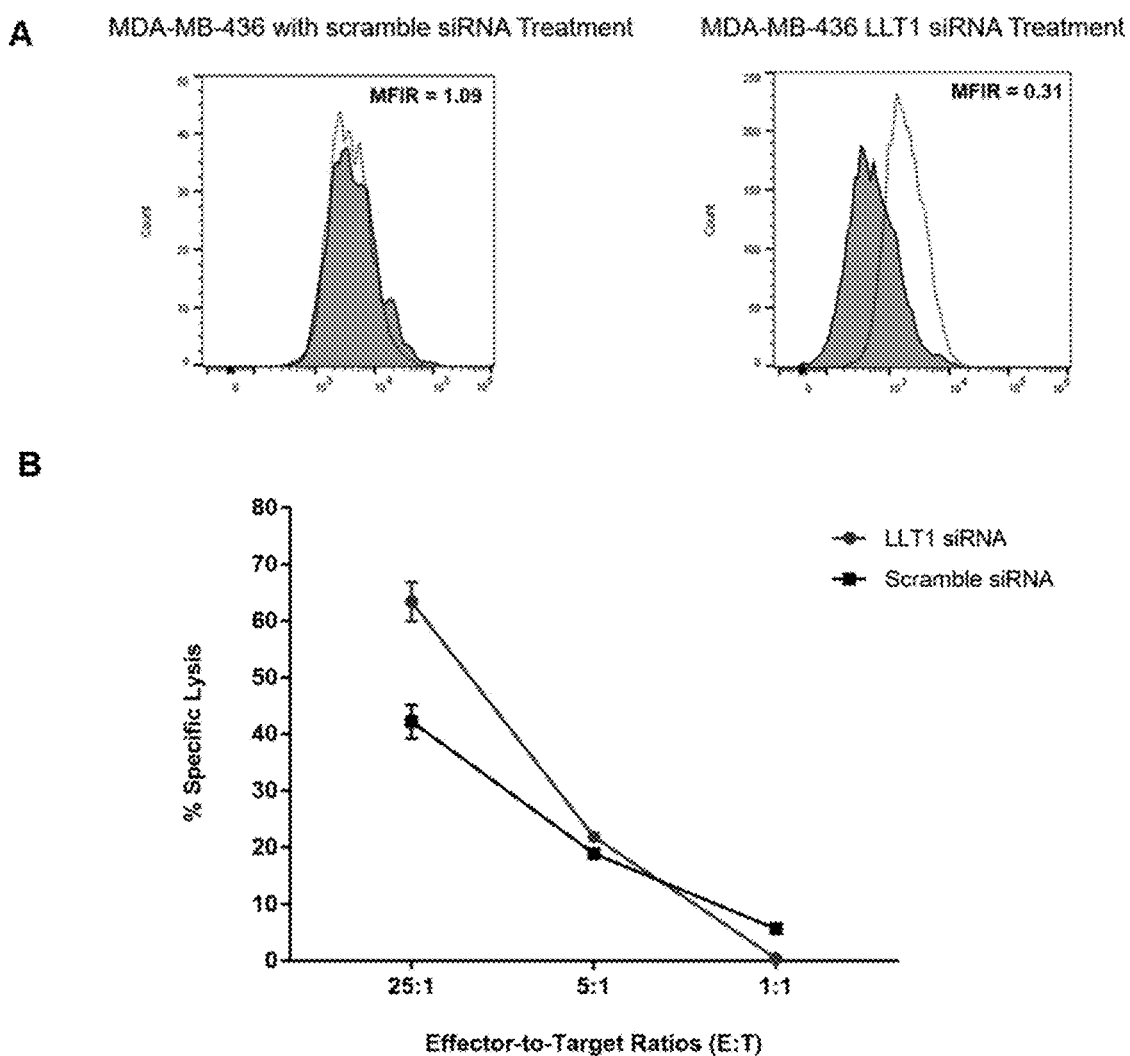
FIGS. 20A-B

COMPOSITIONS AND METHODS FOR ACTIVATION OF NK CELLS KILLING OF PROSTATE CANCER AND BREAST CANCER CELLS

PRIORITY PARAGRAPH

The present application claims priority to U.S. Application No. 62/555,566 filed Sep. 7, 2017, which is incorporated herein by reference in its entirety.

STATEMENT REGARDING FEDERALLY FUNDED RESEARCH

None.

REFERENCE TO SEQUENCE LISTING

The instant application contains a Sequence Listing which has been submitted in ASCII format and is hereby incorporated by reference in its entirety. Said ASCII copy, created on Sep. 7, 2017, is named UTSGP0004US_sequence_listing.txt and is 8,309 bytes in size.

BACKGROUND OF THE INVENTION

A. Field of the Invention

The invention generally concerns compositions and methods for treating cancers expressing Lectin-like transcript 1 (LLT1). In particular the compositions and/or methods include an anti-LLT1 antibody that results in the activation of NK cells.

B. Description of Related Art

Cancer is the second leading cause of death in the United States. More than 80% of the cancer deaths are due to metastasis and relapse after therapy. Prostate cancer (PC) and Breast Cancer (BC) are the most common type of cancer diagnosed in American men and women respectively. Conventional therapies such as surgery, chemotherapy and radiation fail to prevent metastases. Immunotherapy is safe and has shown promise of preventing metastases. Natural Killer (NK) cells are best suited for immunotherapy because of their ability to effectively kill cancer cells.

Current therapy options for cancer treatment are fairly successful as the overall death rates for most cancers have steadily decreased over the last ten years. However, the major problem with cancer arises years later, when the cancer comes back. For many patients, the return of cancer is accompanied with the cancer's spread to another part of the body. Ultimately, the primary cause of mortality in cancer is metastasis, as the primary tumor accounts for only 10% of deaths. Therapy has clearly increased the survival rate after diagnosis, but often fails in the form of complete recovery. Thus, the current therapeutic approach to treating cancer has fundamental flaws. Most pharmaceuticals used in current treatment options target rapidly dividing cells within the tumor, which are terminally differentiated. The problem with current therapies is it fails to address the complexity which makes up a tumor and drives its growth. Breast cancer may metastasize to bones, lung, liver and brain and at present there is no cure for metastatic breast cancer. The use of herceptin or trastuzumab, (monoclonal antibody against human epidermal growth factor receptor 2) has shown some reduction in metastasis. However, herceptin could be used only in 20% of breast cancer (her2 overexpressing) and herceptin can increase the risk of congestive heart failure. Therefore, the need for an effective treatment which could prevent metastasis of breast cancer is highly desirable. Of the many treatment approaches for recurrent prostate cancer that no longer responds to hormonal agents, the emergence of immunotherapy such as immune checkpoint inhibitors and therapeutic cancer vaccines has revolutionized cancer treatment.

SUMMARY OF THE INVENTION

Compositions and methods of the current invention provide a solution to the problems associated with the treatment of cancers overexpressing the LLT1 protein. In particular, inhibition of the expression or interaction of LLT1 expressed on the surface of cancer cells can lead to treatment of the LLT1 expressing cancer cell. By way of example, the inventors have discovered a process to inhibit the interaction between LLT1 and CD161, which results in activation of anti-cancer mediators having appropriate activity to inhibit, ameliorate, or treat cancer in an individual. Without wishing to be bound by theory, it is believed that the use of molecules or proteins that down regulate or inhibit LLT1 results in the treatment of cancers overexpressing LLT1. In certain aspects the anti-LLT1 treatment can be a small molecule or nucleic acid that inhibits transcription, translation, or cell surface expression of LLT1. In other aspects the anti-LLT1 treatment can be an extracellular polypeptide, such as an antibody, that binds and inhibits the function of LLT1.

The inventors have discovered that prostate cancer cells and breast cancer cells express LLT1 surface receptor. Previously, the inventors had shown that LLT1 is a counter-receptor for NK cell inhibitory receptor NKRP1A (CD161). Interaction of LLT1 on PC and BC cells with CD161 on NK cells inhibits NK cell killing activity, thus allowing cancer cells to escape immune surveillance. When the inventors blocked LLT1-CD161 interaction with anti-LLT1 monoclonal antibody (mAb), NK cells killed PC and BC cells. Thus, by blocking the inhibitory signal to NK cells, the inventors could eliminate PC and BC cancer cells.

Certain embodiments are directed to methods for treating cancer comprising administering an effective amount of an anti-LLT1 therapy. In certain aspects the cancer is prostate cancer or breast cancer. In other aspects the anti-LLT1 therapy is an antibody or antibody fragment thereof that binds the extracellular portion of the LLT1 protein. In particular aspects the antibody is a human antibody. In a preferred aspect the antibody is produced by hybridoma 2E5 and 3G1 as described herein. In certain aspects the anti-LLT1 therapy is used in combination with an effective amount of second anti-cancer therapy. In certain aspects the cancer is premalignant, malignant, metastatic, and/or drug-resistant.

In certain aspects the anti-LLT1 therapy is administered about 1, 2, 3, 4, 5, 6, 7, 8, 9, or 10 hours or days prior to administration of a second therapy. In a further aspect the anti-LLT1 therapy is administered simultaneously with a second anti-cancer therapy. In certain aspects the anti-LLT1 therapy and a second therapeutic agent are present in the same pharmaceutical formulation. The pharmaceutical formulations can be administered at approximately the same time. In certain aspects the anti-LLT1 therapy is a monoclonal antibody that specifically binds a LLT1 protein expressed on a target cell and/or blocks the binding of a CD161 protein to LLT1.

As used herein, an "inhibitor" can be any chemical compound, peptide, or polypeptide that can reduce the interaction, binding, activity or function of a protein. An inhibitor as provided by the invention, for example, can inhibit directly or indirectly the activity of a LLT1 protein or interaction thereof with an interacting protein. Direct inhibition can be accomplished, for example, by binding to a LLT1 protein and thereby preventing the protein from binding an intended target, such as a receptor, or by inhibiting an enzymatic or other activity of the protein, either competitively, non-competitively, or uncompetitively. Indirect inhibition can be accomplished, for example, by binding to a protein's intended target, such as a receptor or binding partner, thereby blocking or reducing activity of the protein; or alternatively, inhibiting the expression or presentation of LLT1 on the cells surface.

The phrases "treating cancer" and "treatment of cancer" mean to decrease, reduce, or inhibit the replication of cancer cells; decrease, reduce or inhibit the spread (formation of metastases) of cancer; decrease tumor size; decrease the number of tumors (i.e., reduce tumor burden); lessen or reduce the number of cancerous cells in the body; prevent recurrence of cancer after surgical removal or other anti-cancer therapies; or ameliorate or alleviate the symptoms of the disease caused by the cancer.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa.

The use of the word "a" or "an" when used in conjunction with the term "comprising" in the claims and/or the specification may mean "one," but it is also consistent with the meaning of "one or more," "at least one," and "one or more than one."

The term "about" or "approximately" are defined as being close to as understood by one of ordinary skill in the art. In one non-limiting embodiment the terms are defined to be within 10%, preferably within 5%, more preferably within 1%, and most preferably within 0.5%.

The term "substantially" and its variations are defined to include ranges within 10%, within 5%, within 1%, or within 0.5%.

The term "effective," as that term is used in the specification and/or claims, means adequate to accomplish a desired, expected, or intended result.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods of making and using the same of the present invention can "comprise," "consist essentially of," or "consist of" particular ingredients, components, blends, method steps, etc., disclosed throughout the specification.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

The patent or application file contains at least one drawing executed in color. Copies of this patent or patent application publication with color drawing(s) will be provided by the Office upon request and payment of the necessary fee.

FIGS. 1A-C. Human prostate cancer cells express LLT1. (A) mRNA expression of LLT1 on prostate cancer cell lines PC3, DU145, LNCaP, 22Rv1, normal prostate cell PWR-1E and Jurkat (T cell line) was determined by qRT-PCR. LLT1 expression was determined by using LLT1 sequence specific primers and Taqman gene expression assays in an Eppendorf Realplex2 Mastercycler. Reactions were done in 20 μl triplicates using the ΔΔCT method, with Glyceraldehyde-3-phosphate dehydrogenase (GAPDH) as the reference gene. Each bar represents a mean±s.e. of three independent experiments. (B) LLT1 protein expression was analyzed by Western blotting in a panel of prostate cancer cell lines including leukemic Jurkat cells. GAPDH was used as a loading control. (C) A bar graph showing densitometric analysis of LLT1 protein expression normalized to GAPDH. Each bar represents the mean±s.e. of three independent experiments.

FIG. 4. Prostate cancer tissues show numerous infiltrating lymphocytes. Formalin-fixed and paraffin-embedded prostate cancer (A, C) and normal prostate tissues (B, D) obtained from National Disease Research Interchange (NDRI) were sectioned by standard microtomy procedures and were stained with Haematoxylin and Eosin (H&E) stains. The sections were imaged at 20× and 40× magnifications. Arrows indicate infiltrating lymphocytes.

FIG. 5. Prostate cancer tissues show increased expression of LLT1 as compared to normal prostate tissues. The deparaffinized prostate cancer (A, C) and normal prostate tissue (B, D) sections were processed for antigen retrieval and stained with LLT1 Ab (mouse anti-human CLEC2D Ab, Lifespan Biosciences, Seattle, Wash.) and counter stained with anti-Mouse-IgG-Dylight 594 Ab (red). Sections were also stained with the nuclear stain DAPI (blue) indicated by the blue stain and imaged on an Olympus AX70 fluorescent microscope. Merged images of LLT1 Ab and DAPI are shown. LLT1 expression is indicated by the red/pink stain. The sections were imaged at 20× and 100× magnifications.

FIGS. 6A-E. Blocking LLT1 on prostate cancer cells enhances NK cell-mediated lysis of prostate cancer cells. The cell surface expression of LLT1 on a panel of prostate cancer (A-D) and normal prostate (E) cells was blocked either with a mouse anti-human LLT1 mAb (LLT1) or mouse IgG1 isotype control mAb (cAb) and subsequently labeled with radioactive $^{51}$Cr. The labeled cells were incubated with primary NK cells from a healthy individual and the cytolytic activity was determined by the standard 4 hr radioactive $^{51}$Cr release assay at an Effector to target (E:T) ratios of 25:1, 5:1 and 1:1. Assays were performed in triplicates and the results are representative of two independent experiments. Each data point is the mean value of the repeated experiments and the error bars refer to the means SD generated from the two independent assays. Student's t-test was used to compare cytotoxicity of primary NK cells against prostate cancer cells blocked with LLT1 mAb and the cells incubated with isotype control Ab (mouse IgG1). (*, $p<0.05$; , $p<0.01$; *, $p<0.005$).

FIG. 9. Increased killing of LLT1 specific siRNA treated DU145 cells by NK cells. The cell surface expression of LLT1 on DU145 cells was downregulated by siRNA treatment and subsequently labeled with radioactive $^{51}$Cr. The labeled cells were incubated with primary NK cells from a healthy individual and the cytolytic activity was determined by the standard 4 hr radioactive $^{51}$Cr release assay at an Effector to target (E:T) ratios of 25:1, 5:1 and 1:1. Assays were performed in triplicates and the error bars refer to the means SD generated from the triplicates. Student's t-test was used to compare cytotoxicity of primary NK cells against untreated DU145 cells and the LLT1 siRNA treated. DU145 cells. (*, $p<0.05$; **, $p<0.005$)

FIGS. 10A-B. Flow cytometry analysis demonstrating inhibition of cell surface expression of LLT1 on Breast Cancer cells MDA-MB 231 cells by LLT1 specific siRNA. (A) LLT1 expression on MDA-MB 231 cells without siRNA treatment. Surface expression of LLT1 on MDA-MB 231 cells was determined by flow cytometry using mouse anti-human LLT1 mAb (clone #2E5) and a PE conjugated goat anti-mouse IgG polyclonal secondary antibody. (B) LLT1 expression on MDA-MB 231 after siRNA treatment. All MDA-MB 231 samples were analyzed by flow cytometry analysis 96 hours after transfection. Dotted histogram represents isotype control (mIgG1-PE mAb) staining and filled histogram shows LLT1 expression. MFIR is the mean fluorescence intensity ratio.

FIGS. 16A-B. Triple-negative breast cancer cell lines display a higher expression of LLT1 at the cell surface than normal breast cells. (A) Cell surface expression of LLT1 on TNBC cell lines MDA-MB-231 and MDA-MB-436 and non-tumorigenic breast cell line MCF10A was determined by flow cytometry analysis. Dotted lines represents cells stained with isotype control IgG1-PE antibodies and solid line represents cells stained with anti-LLT1-PE antibodies. (B) Median fluorescence intensity ratios (MFIRs) and percentage of cells displaying positive expression of LLT1 from 3 independent experiments were averaged. * $p<0.05$ & ** $p<0.01$, One-way ANOVA with Dunnett's multiple comparisons post-hoc.

FIGS. 19A-C. Blocking LLT1 on triple-negative breast cancer cells increased lysis of TNBCs by NK cells. A, B, C. Blocking LLT1 at the cell surface of TNBC cell lines MDA-MB-231 and MDA-MB-436 enhanced lysis of these cells by primary NK cells. MCF10A, MDA-MB-231, and MDA-MB-436 were blocked with anti-human LLT1 antibodies (αLLT1 in legend) or goat IgG isotype control antibodies (isotype control in legend). Cells were labeled with $^{51}$Cr and then were co-incubated with primary NK cells at effector-to-target (E:T) ratios of 25:1, 5:1, and 1:1 for 3.5 hours. Specific lysis of cells was subsequently quantified. These assays were performed in triplicates and error bars indicate standard deviations. * p<0.05 & ** p<0.01, Student paired t-test compared to isotype control.

FIGS. 20A-B. Knockdown of LLT1 at the cell surface of triple-negative breast cancer cells increased lysis of TNBCs by NK cells. (A) TNBC cell line MDA-MB-436 was transfected for a period of 63 hours with scramble siRNA control or siRNA targeting LLT1 gene. Knockdown of LLT1 at the cell surface of MDA-MB-436 was confirmed by flow cytometry which displayed negligible expression of LLT1 at the cell surface (MFIR<1.00). MFIR is median fluorescence intensity ratio. (B) Transfected MDA-MB-436 cells with confirmed. LLT1 knockdown at the cell surface were labeled with $^{51}$Cr and co-incubated with primary NK cells at E:T ratios of 25:1, 5:1, and 1:1 for 3.5 hours. Specific lysis of transfected MDA-MB-436 cells killed by NK cells was quantified. This assay was performed in triplicates and error bars represent standard deviations. p=0.07 at 25:1 ratio, Student paired t-test compared to isotype control.

DETAILED DESCRIPTION OF THE INVENTION

Figure 2A:
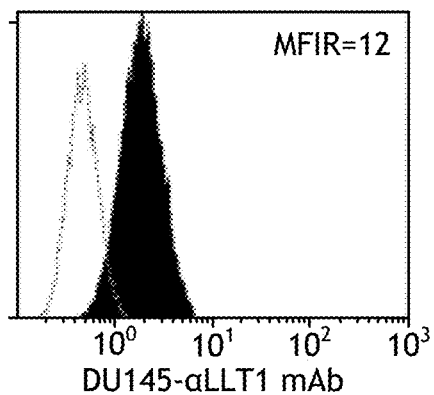
FIGS. 2A-F. Prostate cancer cell lines display increased cell surface expression of LLT1. (A-F) Surface expression of LLT1 on prostate cancer cells DU145, LNCaP, PC3 and 22Rv1, normal prostate cell PWR-1E and Jurkat (T cell line) was determined by flow cytometry using mouse anti-human LLT1 mAb (clone #2E5) and a PE conjugated goat anti-mouse IgG polyclonal secondary antibody. An isotype control antibody (mIgG1-PE mAb) (R&D Systems, Minneapolis, Minn.) was used as negative control. Dotted histogram represents isotype control (mIgG1-PE mAb) staining and filled histogram shows LLT1 expression. MFIR is the mean fluorescence intensity ratio.
Figure 2B:
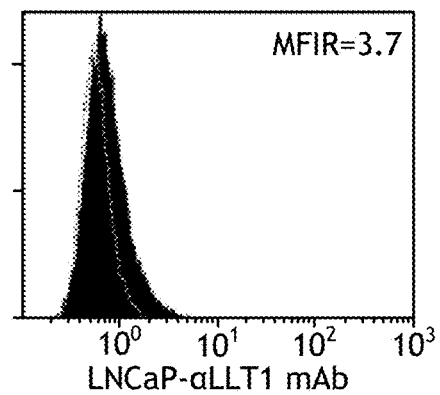
Figure 2C:
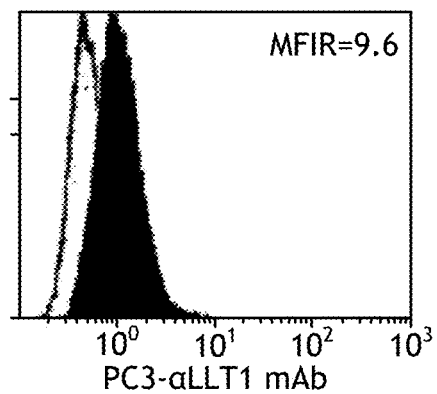
Figure 2D:
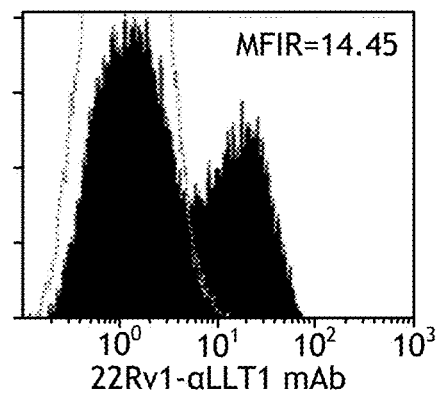
Figure 2E:
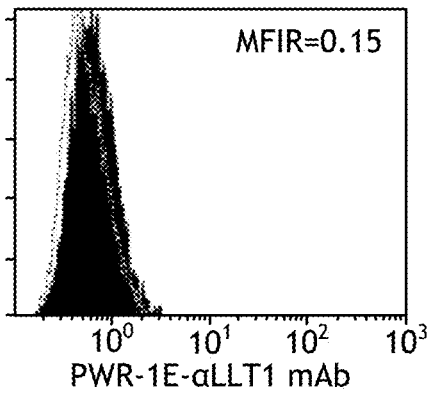
Figure 2F:
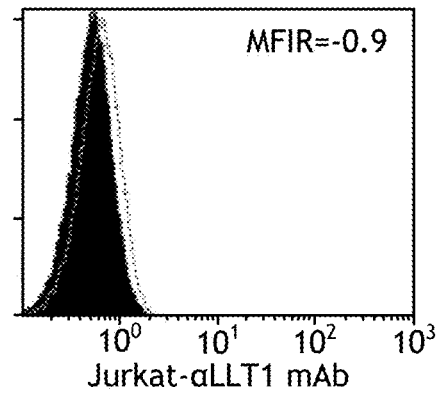

Prostate cancer is the most common type of cancer diagnosed and the second leading cause of cancer-related death in American men. Natural Killer (NK) cells are the first line of defense against cancer and infections. NK cell function is regulated by a delicate balance between signals received through activating and inhibitory receptors. Previously, the inventors identified Lectin-like transcript-1 (LLT1/OCIL/CLEC2D) as a counter-receptor for the NK cell inhibitory receptor NKRP1A (CD161). Interaction of LLT1 expressed on target cells with NKRP1A inhibits NK cell activation. In the study described herein, the inventors have found that LLT1 was overexpressed on prostate cancer cell lines (DU145, LNCaP, 22Rv1 and PC3) and in primary prostate cancer tissues both at the mRNA and protein level. The inventors further showed that LLT1 is retained intracellularly in normal prostate cells with minimal cell surface expression. Blocking LLT1 interaction with NKRP1A by anti-LLT1 mAb on prostate cancer cells increased the NK-mediated cytotoxicity of prostate cancer cells. The results indicate that prostate cancer cells may evade immune attack by NK cells by expressing LLT1 to inhibit NK cell-mediated cytolytic activity through LLT1-NKRP1A interaction. Blocking LLT1-NKRP1A interaction will make prostate cancer cells susceptible to killing by NK cells and therefore may be a new therapeutic option for treatment of prostate cancer or breast cancer.

The therapeutic methods encompassed by the present invention involve primary tumors or cancers, as well as metastases. As an example, a method for inhibiting or killing cancer cells comprises administering to a patient one or more of the monoclonal antibodies having specificity for the cancer cells (LLT1 expressing cancer cells), or a binding fragment thereof, as described above, under conditions sufficient for the binding of the monoclonal antibody, or binding fragment, to tumor or cancer cells in the patient. The binding of antibodies, or their binding fragments, to the tumor cells or cancer cells induces the inhibiting or killing of the cells by the patient's immune cells. Certain methods employ the antibodies or their binding fragments without modification, relying on the binding of the antibodies to the surface of the cancer cells in situ to stimulate and induce an immune response and attack by autologous immune cells thereon.

The anti-LLT1 antibody described herein can be used to kill breast cancer and prostate cancer cells by NK cells. Immunotherapy using monoclonal antibody (mAb) has shown success against several type of cancers. The mechanism of killing of tumor cells by NK cells is based on NK cells recognizing the Fc region of mAb bound to the cancer cell and getting activated (called ADCC-antibody dependent cell mediated cytotoxicity). The anti-LLT1 mAb will activate NK cells in two different ways—(i) by blocking LLT1-CD161 interaction, it will activate NK cells for killing (natural cytotoxicity), and/or (ii) the Fc region of LLT1 mAb will be recognized by CD16 on NK cells and activate ADCC. The inventor's previous anti-CS1 mAb (Elotuzumab or Empliciti by BMS) activates natural cytotoxicity and ADCC by NK cells and has proven a breakthrough drug against multiple myeloma. The inventors believe anti-LLT1 mAb will have advantages over other mAb that are currently in use against Breast cancer (Herceptin) or Prostate cancer (anti-PSA mAb). Moreover, anti-LLT1 mAb could be used against her2 negative BC.

Prostate cancer (PC) is the most frequently diagnosed cancer and the second leading cause of cancer-related death in American men [1]. Although, the majority of patients are treated successfully with radical prostatectomy or radiation therapy, approximately 30-40% of patients will ultimately develop recurrent disease [2]. Apart from the hallmarks of cancer that enable cancer cells to become tumorigenic and ultimately malignant, an increasing body of research suggests that there is active evasion by cancer cells from attack and elimination by immune cells [3]. Of the many treatment approaches for recurrent prostate cancer that no longer responds to hormonal agents, the emergence of immunotherapy such as immune checkpoint inhibitors and therapeutic cancer vaccines has revolutionized cancer treatment [4]. Prostate cancer is an excellent tumor target for immune-based therapies as it has an indolent disease course, which allows the immune system to generate an immune response. In addition, prostate specific antigen (PSA) allows for detection of disease when the cancer is at the micro-metastatic level, allowing for small volumes of disease to be treated.

Natural killer (NK) cells are bone marrow derived lymphocytes that play important role against cancer and various infections [5-7]. NK cells have the capacity to kill virusinfected or tumor-transformed cells and to produce immunoregulatory cytokines without the need of prior sensitization of their targets [8]. NK cells express several surface molecules that regulate NK cell function both positively and negatively and that it is the sum of these signals that ultimately determines cell function and activation [5, 9-11]. NK cells are major producers of cytokines including interferon (IFN)-γ, tumor necrosis factor (TNF)-α, and granulocyte-macrophage-colony stimulating factors (GM-CSF) and interleukin (IL)-3 [12]. Several cytokines such as IL-2, IL-4, IL-7, IL-12, IFNγ, and IFNα, and various drugs such as tamoxifen, toremifene and levamisole, have been used either directly to the patient or cultured with lymphokine-activated killer (LAK) cells in attempts to halt and reverse various tumor growths [13-17]. These studies have been met with mixed success. A 11-year follow-up pioneering study in human population reported that a low degree of NK cell cytotoxicity was correlated with increased cancer risk [18]. Recently, it was reported that NK cell receptors could be potential predictive biomarkers to stratify patients who are likely to have longer castration response in metastatic prostate cancer patients [19].

Lectin-like transcript 1 (LLT1, gene CLEC2D) or osteoclast inhibitory lectin (OCIL) is a type II transmembrane receptor belonging to the C-type lectin like (CTL) superfamily of natural killer cell receptors [20, 21]. LLT1 is expressed mainly on activated lymphocytes (NK cells, T cells, B cells) and antigen presenting cells, i.e., macrophages and dendritic cells [22]. LLT1 was identified as a physiological ligand of NKRP1A, the sole described representative of the human NKR-P1 subfamily (CD161, gene KLRB1) [23, 24]. Six alternatively spliced transcripts of the CLEC2D gene have been identified, with isoform 1 (coding for LLT1) being the only one able to interact with NKRP1A [25]. It is well established that interaction between NKRP1A on NK cells and LLT1 on target cells leads to inhibition of NK cell mediated cytotoxic response [23, 24, 26] and contributes to NK self-tolerance in a similar way to the orthologous rodent NKR-P1B-Clr-b receptor-ligand pair [27, 28]. Cross-linking of LLT1 on NK cells by a monoclonal antibody induces interferon gamma secretion by NK cells involving the ERK signaling pathway [21, 29]. It has been shown that human glioblastoma exploits this mechanism by the upregulation of the surface expression of LLT1 to escape the immunological response [30]. On the other hand, LLT1 is upregulated in response to both microbial and viral stimuli, and stimulation of NKR-P1-expressing T cells promotes their activation, proliferation and cytokine secretion [22, 31, 32]. LLT1 was also found to be expressed by cells of the monocyte/macrophage lineage rheumatoid arthritis (RA) patients and serum levels of soluble LLT1 were increased in all patient groups (patients with early- and late-stage RA, seropositive arthralgia and spondyloarthropathy) when compared to healthy subjects [33].

In the study described herein, the inventors observed LLT1 expression on hormone-refractory prostate cancer cell lines DU145, PC3, 22Rv1, hormone-sensitive LNCaP cells normal prostate cells PWR-1E and acute T leukemia cell Jurkat both at the mRNA and protein level. All the prostate cancer lines showed high expression of LLT1 both at mRNA and protein level. Interestingly, the inventors showed that LLT1 is retained intracellularly in normal prostate cells with minimal cell surface expression whereas it is highly overexpressed on the cell surface of PC3 cells. High expression of LLT1 was also observed in tissues obtained from prostate cancer patients. Blocking LLT1 on prostate cancer cells by anti-human LLT1 mAb increased the NK-mediated cytotoxicity of prostate cancer cells. The inventors suggest that blocking LLT1-NKRP1A interaction will make prostate cancer cells susceptible to killing by NK cells and therefore may be a new therapeutic option for treatment of prostate cancer.

A. Anti-LLT1 Compositions

Anti-LLT1 composition can include molecules, nucleic acids, and/or polypeptides that inhibit or reduce the cell surface expression and/or activity of LLT1. In certain aspects the anti-LLT1 composition includes inhibitory nucleic acids and/or anti-LLT1 antibodies.

The term "antibody" or "immunoglobulin" is used to include intact antibodies and binding fragments/segments thereof. Typically, fragments compete with the intact antibody from which they were derived for specific binding to an antigen. Fragments include separate heavy chains, light chains, Fab, Fab' F(ab')2, Fabc, and Fv. Fragments/segments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes bispecific antibodies. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai and Lachmann, *Clin Exp Immunol* 79:315-21, 1990; Kostelny et al., J. Immunol. 148:1547-53, 1992.

The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized). Moreover, an isolated compound refers to one that can be administered to a subject as an isolated compound; in other words, the compound may not simply be considered "isolated" if it is adhered to a column or embedded in an agarose gel. Moreover, an "isolated nucleic acid fragment" or "isolated peptide" is a nucleic acid or protein fragment that is not naturally occurring as a fragment and/or is not typically in the functional state.

"Antibody" refers to all isotypes of immunoglobulins (IgG, IgA, IgE, IgM, and IgY) including various monomeric and polymeric forms of each isotype, unless otherwise specified.

"Functional fragments" of such antibodies comprise portions of intact antibodies that retain binding specificity of the parent antibody molecule. For example, functional fragments can comprise at least the CDRs of either the heavy chain and/or light chain variable region. Functional fragments can also comprise the heavy chain or light chain variable region, or sequences that are substantially similar to the heavy or light chain variable region. Further suitable functional fragments include, without limitation, antibodies with multiple epitope specificity, bispecific antibodies, diabodies, and single-chain molecules, as well as Fab, F(ab')2, Fd, Fabc, and Fv molecules, single chain (Sc) antibodies (also called ScFv), individual antibody light chains, individual antibody heavy chains, chimeric fusions between antibody chains and other molecules, heavy chain monomers or dimers, light chain monomers or dimers, dimers consisting of one heavy and one light chain, and the like. All antibody isotypes can be used to produce functional fragments of the antibodies described herein. Functional fragments can be recombinantly or synthetically produced.

The antibodies or functional fragments thereof of the disclosed subject matter can be generated from any species. The antibodies or functional fragments thereof described herein can be labeled or otherwise conjugated to various chemical or biomolecule moieties (heterologous moieties), for example, for therapeutic or diagnostic or detection or treatment applications. The moieties can be cytotoxic, for example, bacterial toxins, viral toxins, radioisotopes, and the like. The moieties can be detectable labels, for example, fluorescent labels, radiolabels, biotin, and the like, which are known in the art.

The antibody or functional fragment can be labeled with fluorophores. There are a wide variety of fluorophore labels that can usefully be attached to the antibodies of the present invention. For flow cytometric applications, both for extracellular detection and for intracellular detection, common useful fluorophores can be fluorescein isothiocyanate (FITC), allophycocyanin (APC), R-phycoerythrin (PE), peridinin chlorophyll protein (PerCP), Texas Red, Cy3, Cy5, fluorescence resonance energy tandem fluorophores such as PerCPCy5.5, PE-Cy5, PE-Cy5.5, PE-Cy7, PE-Texas Red, and APC-Cy7. Other fluorophores include, inter alia, Alexa Fluor® 350, Alexa Fluor® 488, Alexa 25 Fluor® 532, Alexa Fluor® 546, Alexa Fluor® 568, Alexa Fluor® 594, Alexa Fluor® 647 (monoclonal antibody labeling kits available from Molecular Probes, Inc., Eugene, Oreg., USA), BODIPY dyes, such as BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Molecular Probes, Inc., Eugene, Oreg., USA), and Cy2, Cy3, Cy3.5, Cy5, Cy5.5, Cy7, all of which are also useful for fluorescently labeling the antibodies of the present invention. For secondary detection using labeled avidin, streptavidin, captavidin or neutravidin, the antibodies of the present invention can usefully be labeled with biotin. When the antibodies of the present invention are used, e.g., for western blotting applications, they can usefully be labeled with radioisotopes, such as 33P, 32P, 35S, 3H, and 125I. As another example, when the antibodies of the present invention are used for radioimmunotherapy, the label can usefully be 3H, 228Th, 227Ac, 225Ac, 223Ra, 213Bi, 212Pb, 212Bi, 211At, 203Pb, 1940s, 188Re, 186Re, 153Sm, 149Tb, 131I, 125I, 111In, 105Rh, 99mTc, 97Ru, 90Y, 90Sr, 88Y, 72Se, 67Cu, or 47Sc.

"Derived from" can mean a polypeptide resulting from methods of derivation. "Derived from" includes the use of algorithms for designing and testing antibody binding, creating a functionally equivalent antibody or fragment thereof that retains the binding and/or specificity of the parent antibody. "Derived from" contemplates the use of antibodies having substantially similar amino acid or nucleotide sequences (at least or about 80, 85, 90, 95, 98, 99% identical, including all values and ranges there between) to a parent antibody, such as 2E5 or 3G1 mAb.

The antibodies and functional fragments thereof described herein bind lectin-like transcript 1 (LLT1), amino acid sequence of SEQ ID NO: 1. LLT1 is expressed on the surface of activated immune cells, such as B, T, NK, and dendritic cells, but is absent from resting, naïve cells. The receptor for LLT1 is CD161, also known as NKRP1A. CD161 is found on NK cells and effector/memory T cells. In T cells, the CD161 receptor functions as a co-stimulator of TCR signaling, whereas in NK cells CD161 is a cytotoxicity inhibitory receptor that restricts killing of cells expressing the CD161-ligand, LLT1.

An "anti-LLT1 antibody" described herein binds LLT1 and inhibits CD161 inhibition of NK cell activity. An "anti-LLT1 antibody" includes the 2E5 or 3G1 mAb, an antibody comprising a light chain variable region of 2E5 or 3G1 and a heavy chain variable region 2E5 or 3G1. An "anti-LLT1 antibody" includes an antibody comprising a light chain variable region and/or a heavy chain variable region. An "anti-LLT1 antibody" can comprise the CDRs identified herein. An "anti-LLT1 antibody" includes an antibody comprising a heavy chain variable region of 2E5 or 3G1, or the complementarity-determining regions (CDRs) identified therein.

```
Heavy chain variable region sequence of 2E5
                                         (SEQ ID NO: 2)
EVQLQQSGADLVKPGASVKLSCTASGFNIKDTYMHWVIQRPEQGLDWIGR
IDPANGNTNYDPKFRAKATITADTSSNTAYLQLSSLTSDDTAVYYCAGMD
YHFDFWGQGTTLTVSS, with CDR1, 2 and 3 being
                                         (SEQ ID NO: 3)
GFNIKDTY, (SEQ ID NO: 4)
IDPANGNT
and (SEQ ID NO: 5)
AGMDYHFD, respectively.

Light chain variable region sequence of 2E5
                                         (SEQ ID NO: 6)
DIVMTQSPATLSVTPGDRVSLSCRASQSISDYLHWYQQKSHESPRLLIKY
ASQSISGIPSRFSGSGSGSDFTLSINSVEPEDVGVFYCQNGHSFPLTFGA
GTKLELRR with CDR1, 2 and 3 being
                                         (SEQ ID NO: 7)
QSISDY, (SEQ ID NO: 8)
YAS
and (SEQ ID NO: 9)
QNGHSFPL, respectively.

Heavy chain variable region sequence of 3G1
                                         (SEQ ID NO: 10)
EVQLQQSGPELVKPGASVKISCKASGYSFTGNYMHWVKQSPENSLEWIGE
INIRTGYISYNQKFKGKATLTVDKSSSTAYMQLKSLTSEESAVYYCTRSA
YWGQGTLVTVSA, with CDR1, 2 and 3 being
                                         (SEQ ID NO: 11)
GYSFTGNY, (SEQ ID NO: 12)
INIRTGY
and (SEQ ID NO: 13)
TRSAY, respectively.
```

-continued

Light chain variable region sequence of 3G1
(SEQ ID NO: 14)
DIKMTQSPSSMYTSLGERVTITCKASQDIKSYLSWFQQKPGKSPKTLIYR
ANRLGDGVPSRVSGSGSGQDYSLTIGSLEYEDMGWYCLQYAEFPRTFGGG
TKLEIRR with CDR1, 2 and 3 being
(SEQ ID NO: 15)
QDIKSY, (SEQ ID NO: 16)
RAN
and (SEQ ID NO: 17)
LQYAEFPRT, respectively The antibodies or functional fragments thereof described herein have binding affinities (in M) for LLT1 that include a dissociation constant (KD) of less than $1\times10^{-2}$. In some embodiments, the KD is less than $1\times10^{-3}$. In other embodiments, the KD is less than $1\times10^{-4}$. In some embodiments, the KD is less than $1\times10^{-5}$. In still other embodiments, the KD is less than $1\times10^{-6}$, $2\times10^{-6}$, $3\times10^{-6}$, $4\times10^{-6}$, $5\times10^{-6}$, $6\times10^{-6}$, $7\times10^{-6}$, $8\times10^{-6}$, or $9\times10^{-6}$. In other embodiments, the KD is less than $1\times10^{-7}$, $2\times10^{-7}$, or $3\times10^{-7}$, $2\times10^{-7}$, $3\times10^{-7}$, $4\times10^{-7}$, $5\times10^{-7}$, $6\times10^{-7}$, $7\times10^{-7}$, $8\times10^{-7}$, or $9\times10^{-7}$. In other embodiments, the KD is less than $1\times10^{-8}$, $2\times10^{-8}$, $3\times10^{-8}$, $4\times10^{-8}$, $5\times10^{-8}$, $6\times10^{-8}$, $7\times10^{-8}$, $8\times10^{-8}$, or $9\times10^{-8}$. In other embodiments, the KD is less than $1\times10^{-9}$, $2\times10^{-9}$, $3\times10^{-9}$, $4\times10^{-9}$, $5\times10^{-9}$, $6\times10^{-9}$, $7\times10^{-9}$, $8\times10^{-9}$, or $9\times10^{-9}$. In other embodiments, the KD is less than $1\times10^{-10}$, $2\times10^{-10}$, $3\times10^{-10}$, $2\times10^{-10}$, $3\times10^{-10}$, $4\times10^{-10}$, $5\times10^{-10}$, $6\times10^{-10}$, $7\times10^{-10}$, $8\times10^{-10}$, or $9\times10^{-10}$. In still other embodiments, the KD is less than $1\times10^{-11}$, $2\times10^{-11}$, $3\times10^{-11}$, $4\times10^{-11}$, $5\times10^{-11}$, $6\times10^{-11}$, $7\times10^{-11}$, $8\times10^{-11}$, $9\times10^{-11}$, $1\times10^{-12}$, $1\times10^{-13}$, $1\times10^{-14}$, or $1\times10^{-15}$.

The terms "treating" or "treatment" refer to any success or indicia of success in the attenuation or amelioration of a pathology or condition, including any objective or subjective parameter such as abatement, remission, diminishing of symptoms, or making the pathology or condition more tolerable to the patient, slowing in the rate of progression, improving a subject's physical or mental well-being, or prolonging the length of survival. The treatment or amelioration of symptoms can be based on objective or subjective parameters; including the results of a physical examination, neurological examination, and/or psychiatric evaluations.

"Effective amount" and "therapeutically effective amount" are used interchangeably and refer to an amount of an antibody or functional fragment thereof that achieves a particular biological or therapeutic result such as, but not limited to, the biological or therapeutic results disclosed or described herein. A therapeutically effective amount of the antibody or functional fragment thereof may vary according to factors such as the disease state, age, sex, and weight of the individual, and the ability of the antibody or functional fragment thereof to elicit a desired response in the individual. Such results may include, but are not limited to, the treatment of cancer, as determined by any means suitable in the art.

The term "providing" is used according to its ordinary meaning "to supply or furnish for use." In some embodiments, the protein is provided directly by administering the protein, while in other embodiments, the protein is effectively provided by administering a nucleic acid that encodes the protein. In certain aspects the invention contemplates compositions comprising various combinations of nucleic acid and/or polypeptides:

The phrase "specifically binds" or "specifically immunoreactive" to a target refers to a binding reaction that is determinative of the presence of the molecule in the presence of a heterogeneous population of other biologics. Thus, under designated immunoassay conditions, a specified molecule binds preferentially to a particular target and does not bind in a significant amount to other biologics present in the sample. Specific binding of an antibody to a target under such conditions requires the antibody be selected for its specificity to the target. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane, Antibodies: A Laboratory Manual, Cold Spring Harbor Press, 1988, for a description of immunoassay formats and conditions that can be used to determine specific immunoreactivity.

The term "metastasis" refers to the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system. The cells of a secondary or metastatic tumor are derived from cells in the original tumor. This means, for example, that, if ovarian cancer metastasizes to the liver, the secondary tumor is made up of abnormal ovarian cells, not of abnormal liver cells. The tumor in the liver is then called metastatic ovarian cancer, not liver cancer.

The term "antibody" refers to a protein comprising at least two heavy (H) chains and two light (L) chains inter-connected by disulfide bonds, or an antigen binding portion thereof. The term "antibody" also includes all recombinant forms of antibodies as described herein, e.g., antibodies expressed in prokaryotes, unglycosylated antibodies, and any antigen-binding antibody fragments and derivatives as described herein. Each heavy chain is comprised of a heavy chain variable region (abbreviated herein as $V_H$) and a heavy chain constant region. Each light chain is comprised of a light chain variable region (abbreviated herein as $V_L$) and a light chain constant region. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyterminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "human antibody", as used herein, is intended to include antibodies having variable and constant regions derived from human germ line immunoglobulin sequences.

Human antibodies are well-known in the state of the art (van Dijk, M. A., and van de Winkel, J. G., *Curr. Opin. Chem. Biol.* 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al., *Proc. Natl. Acad. Sci. USA* 90 (1993) 2551-2555; Jakobovits, A., et al., *Nature* 362 (1993) 255-258; Bruggemann, M., et al., *Year Immunol.* 7 (1993) 33-40). Human antibodies can also be produced in phage display libraries (Hoogenboom, H. R., and Winter, G. *J. Mol. Biol.* 227 (1992) 381-388; Marks, J. D., et al., *J. Mol. Biol.* 222 (1991) 581-597). The techniques of Cole et al. and Boerner et al. are also available for the preparation of human monoclonal antibodies (Cole et al., *Monoclonal Antibodies and Cancer Therapy*, Alan R. Liss, p. 77 (1985); and Boerner, P., et al., *J. Immunol.* 147 (1991) 86-95).

The term "humanized antibody" refers to a molecule having an antigen binding site that is derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate human framework regions in the variable domains. Antigen binding sites may be wild-type or modified by one or more amino acid substitutions, e.g., modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

The term "chimeric antibody" refers to those antibodies wherein one portion of each of the amino acid sequences of heavy and light chains is identical to corresponding sequences in antibodies derived from a particular species or belonging to a particular class, while the remaining segment of the chain is related to corresponding sequences of another species or class. Typically the variable region of both light and heavy chains mimics the variable regions of antibodies derived from one species of mammals, while the constant portions are derived from other antibodies. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human, is less likely to elicit an immune response from a human subject when the antibodies are injected. However the definition is not limited to this particular example.

The term "antigen-binding portion" of an antibody (or simply "binding portion"), as used herein, refers to one or more fragments of an antibody that retain the ability to specifically bind to a target. It has been shown that the binding function of an antibody can be performed by fragments of a full-length antibody. Examples of binding fragments encompassed within the term "binding portion" of an antibody include (i) Fab fragments, monovalent fragments consisting of the $V_L$, $V_H$, $C_L$ and $C_H$ domains; (ii) F(ab') 2 fragments, bivalent fragments comprising two Fab fragments linked by a disulfide bridge at the hinge region; (iii) Fd fragments consisting of the $V_H$ and $C_H$ domains; (iv) Fv fragments consisting of the $V_L$ and $V_H$ domains of a single arm of an antibody, (v) dAb fragments (Ward et al., (1989) *Nature* 341:544-46), which consist of a $V_H$ domain; (vi) isolated complementarity determining regions (CDR), and (vii) combinations of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-26; and Huston et al. (1988) *PNAS USA* 85: 5879-83). Such single chain antibodies are also intended to be encompassed within the term "binding portion" of an antibody. A further example is binding-domain immunoglobulin fusion proteins comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region.

The term "epitope" means a protein determinant capable of binding to an antibody, wherein the term "binding" herein preferably relates to a specific binding. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

The term "discontinuous epitope" as used herein, means a conformational epitope on a protein antigen which is formed from at least two separate regions in the primary sequence of the protein.

The term "bispecific molecule" is intended to include any agent, e.g., a protein, peptide, or protein or peptide complex, which has two different binding specificities. For example, the molecule may bind to, or interact with (a) a cell surface antigen, and (h) an Fc receptor on the surface of an effector cell. The term "multispecific molecule" or "heterospecific molecule" is intended to include any agent, e.g., a protein, peptide, or protein or peptide complex, which has more than two different binding specificities. For example, the molecule may bind to, or interact with (a) a cell surface antigen, (b) an Fc receptor on the surface of an effector cell, and (c) at least one other component. Accordingly, the invention includes, but is not limited to, bispecific, trispecific, tetraspecific, and other multispecific molecules. The term "bispecific antibodies" also includes diabodies. Diabodies are bivalent, bispecific antibodies in which the $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, Holliger et al. (1993) *PNAS USA* 90: 6444-48; Poljak et al. (1994) *Structure* 2:1121-23).

The invention also includes derivatives of the antibodies described herein which for the purposes of the invention are encompassed by the term "antibody." The term "antibody derivatives" refers to any modified form of an antibody, e.g., a conjugate of the antibody and another agent or antibody.

As used herein, the term "heteroantibodies" refers to two or more antibodies, derivatives thereof, or antigen binding regions linked together, at least two of which have different specificities. These different specificities include a binding specificity for an Fc receptor on an effector cell, and a binding specificity for an antigen or epitope on a target cell, e.g., a tumor cell.

The antibodies described herein may be human antibodies. The term "human antibody," as used herein, is intended to include antibodies having variable and constant regions derived from human immunoglobulin sequences.

The term "monoclonal antibody" as used herein refers to a preparation of antibody molecules of single molecular composition. A monoclonal antibody displays a single binding specificity and affinity for a particular epitope. In one embodiment, the monoclonal antibodies are produced by a hybridoma which includes a B cell obtained from a non-human animal, e.g., mouse, fused to an immortalized cell.

The term "recombinant antibody," as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, (c) antibodies isolated from a recombinant, combinatorial antibody library, and (d) antibodies prepared, expressed, created or isolated by any other means that involve splicing of immunoglobulin gene sequences to other DNA sequences.

The term "binding" according to the invention relates to a specific binding. "Specific binding" means that an agent such as an antibody binds stronger to a (predetermined) target such as an antigen or an epitope for which it is specific compared to the binding to another target. An agent binds stronger to a first target compared to a second target if it binds to the first target with a dissociation constant (KD) which is lower than the dissociation constant for the second target. In certain aspects the dissociation constant (KD) for the target to which the agent binds specifically is more than 10-fold, preferably more than 20-fold, more preferably more than 50-fold, even more preferably more than 100-fold, 200-fold, 500-fold or 1000-fold lower than the dissociation constant (KD) for the target to which the agent does not bind specifically. Typically, the antibody binds with an affinity corresponding to a KD of about $1 \times 10^{-7}$ NI or less, and binds to the predetermined antigen with an affinity corresponding to a KD that is at least two orders of magnitude lower than its affinity for binding to a non-specific antigen (e.g., BSA, casein) other than the predetermined antigen or a closely-related antigen.

As used herein, "isotype" refers to the antibody class (e.g., IgM or IgG1) that is encoded by heavy chain constant region genes.

As used herein, "isotype switching" refers to the phenomenon by which the class, or isotype, of an antibody changes from one Ig class to one of the other Ig classes.

The teaching given herein with respect to specific amino acid sequences, e.g., those shown in the sequence listing, is to be construed so as to also relate to modifications of the specific sequences resulting in sequences which are functionally equivalent to the specific sequences, e.g., amino acid sequences exhibiting properties identical or similar to those of the specific amino acid sequences. Similarly, the teaching given herein with respect to specific antibodies or hybridomas producing specific antibodies is to be construed so as to also relate to antibodies characterized by an amino acid sequence and/or nucleic acid sequence which is modified compared to the amino acid sequence and/or nucleic acid sequence of the specific antibodies but being functionally equivalent. One important property is to retain binding of an antibody to its target or to sustain effector functions of an antibody. Preferably, a sequence modified with respect to a specific sequence, when it replaces the specific sequence in an antibody retains binding of said antibody to LLT1 and preferably functions as described herein.

It will be appreciated by those skilled in the art that in particular the sequences of the CDR, hypervariable and variable regions can be modified without losing the ability to bind LLT1. For example, CDR regions will be either identical or highly homologous to the regions of antibodies specified herein. By "highly homologous" it is contemplated that from 1 to 5, preferably from 1 to 4, such as 1 to 3 or 1 or 2 substitutions may be made in the CDRs. In addition, the hypervariable and variable regions may be modified so that they show substantial homology with the regions of antibodies specifically disclosed herein.

Furthermore, it may be desired according to the present invention to modify the amino acid sequences described herein, in particular those of human heavy chain constant regions to adapt the sequence to a desired allotype.

According the invention, the term "corresponding positions" relates to amino acid residues which in a sequence alignment of two protein sequences are aligned to each other. According to the invention, a variant, derivative, modified form or fragment of an amino acid sequence or peptide preferably has a functional property of the amino acid sequence or peptide, respectively, from which it has been derived. Such functional properties comprise the interaction with or binding to other molecules. In one embodiment, a variant, derivative, modified form or fragment of an amino acid sequence or peptide is immunologically equivalent to the amino acid sequence or peptide, respectively, from which it has been derived.

For the purposes of the present invention, "variants" of an amino acid sequence comprise amino acid insertion variants, amino acid deletion variants and/or amino acid substitution variants. Preferably the degree of similarity, preferably identity between a specific amino acid sequence and an amino acid sequence which is modified with respect to or which is a variant of said specific amino acid sequence such as between amino acid sequences showing substantial homology will be at least 70%, 80%, 90%, 95%, 96%, 97%, 98% or 99%. In certain embodiments, the degree of similarity or identity is given for the entire length of the reference amino acid sequence such as the amino acid sequences given in the sequence listing, or optionally over a specific segment of a polypeptide.

"Sequence similarity" indicates the percentage of amino acids that either are identical or that represent conservative amino acid substitutions. "Sequence identity" between two polypeptide or nucleic acid sequences indicates the percentage of amino acids or nucleotides that are identical between the sequences.

The "percentage identity" is obtained after the best alignment, this percentage being purely statistical and the differences between the two sequences being distributed randomly and over their entire length. Sequence comparisons between two nucleotide or amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl. Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.). The percentage identity is calculated by determining the number of identical positions between the two sequences being compared, dividing this number by the number of positions compared and multiplying the result obtained by 100 so as to obtain the percentage identity between these two sequences.

"Conservative substitutions," may be made, for instance, on the basis of similarity in polarity, charge, solubility, hydrophobicity, hydrophilicity, and/or the amphipathic nature of the residues involved. For example: (a) nonpolar (hydrophobic) amino acids include alanine, leucine, isoleucine, valine, proline, phenylalanine, tryptophan, and methionine; (b) polar neutral amino acids include glycine, serine, threonine, cysteine, tyrosine, asparagine, and glutamine; (c) positively charged (basic) amino acids include arginine, lysine, and histidine; and (d) negatively charged (acidic) amino acids include aspartic acid and glutamic acid. Substitutions typically may be made within groups (a)-(d). In addition, glycine and proline may be substituted for one another based on their ability to disrupt α-helices. Some preferred substitutions may be made among the following groups: (i) S and T; (ii) P and G; and (iii) A, V, L and I. Given the known genetic code, and recombinant and synthetic DNA techniques, the skilled scientist readily can construct DNAs encoding the conservative amino acid variants.

"Reduce" or "inhibit" as used herein means the ability to cause an overall decrease, preferably of 5% or greater, 10% or greater, 20% or greater, more preferably of 50% or greater, and most preferably of 75% or greater, in the level, e.g. in the level of proliferation of cells.

B. Production of Antibodies

Antibodies of the invention can be produced by a variety of techniques, including conventional monoclonal antibody methodology, e.g., the standard somatic cell hybridization technique of Kohler and Milstein, Nature 256: 495 (1975). Although somatic cell hybridization procedures are preferred, in principle, other techniques for producing monoclonal antibodies can be employed, e.g., viral or oncogenic transformation of B-lymphocytes or phage display techniques using libraries of antibody genes.

The preferred animal system for preparing hybridomas that secrete monoclonal antibodies is the murine system. Hybridoma production in the mouse is a very well established procedure. Immunization protocols and techniques for isolation of immunized splenocytes for fusion are known in the art. Fusion partners (e.g., murine myeloma cells) and fusion procedures are also known. Other preferred animal systems for preparing hybridomas that secrete monoclonal antibodies are the rat and the rabbit system (e.g., described in Spieker-Polet et al., *PNAS U.S.A.* 92:9348 (1995)).

Yet another strategy for generating monoclonal antibodies is to directly isolate genes encoding antibodies from lymphocytes producing antibodies, e.g., see Babcock et al., 1996; A novel strategy for generating monoclonal antibodies from single, isolated lymphocytes producing antibodies of defined strategy. For details of recombinant antibody engineering see also Welschof and Kraus, Recombinant antibodies for cancer therapy ISBN-0-89603-918-8 and Benny K. C. Lo Antibody Engineering ISBN 1-58829-092-1.

Immunizations.

To generate antibodies to LLT1, mice can be immunized with carrier-conjugated peptides derived from the LLT1 sequence. Alternatively, mice can be immunized with DNA encoding full length human LLT1 (e.g., SEQ ID NO:1) or fragments thereof. The immune response can be monitored over the course of the immunization protocol with plasma and serum samples being obtained by tail vein or retroorbital bleeds. Mice with sufficient titers of anti-LLT1 immunoglobulin can be used for fusions. Mice can be boosted intraperitonealy or intravenously with LLT1 expressing cells 3 days before sacrifice and removal of the spleen to increase the rate of specific antibody secreting hybridomas.

Generation of Hybridomas Producing Monoclonal Antibodies.

To generate hybridomas producing monoclonal antibodies to LLT1, splenocytes and lymph node cells from immunized mice can be isolated and fused to an appropriate immortalized cell line, such as a mouse myeloma cell line. The resulting hybridomas can then be screened for the production of antigen-specific antibodies. Individual wells can then be screened by ELISA for antibody secreting hybridomas. By Immunofluorescence and FACS analysis using LLT1 expressing cells, antibodies with specificity for LLT1 can be identified. The antibody secreting hybridomas can be replated, screened again, and if still positive for anti-LLT1 monoclonal antibodies can be subcloned by limiting dilution. The stable subclones can then be cultured in vitro to generate antibody in tissue culture medium for characterization.

Isolation and Characterization of Antibodies.

To purify anti-LLT1 antibodies, selected hybridomas can be grown in two-liter spinner-flasks for monoclonal antibody purification. Alternatively, anti-LLT1 antibodies can be produced in dialysis based bioreactors. Supernatants can be filtered and, if necessary, concentrated before affinity chromatography with protein G-sepharose or protein A-sepharose. Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

Isotype Determination.

To determine the isotype of purified antibodies, isotype ELISAs with various commercial kits (e.g., Zymed, Roche Diagnostics) can be performed. Wells of microtiter plates can be coated with anti-mouse Ig. After blocking, the plates are reacted with monoclonal antibodies or purified isotype controls, at ambient temperature for two hours. The wells can then be reacted with either mouse IgG1, IgG2a, IgG2b or IgG3, IgA or mouse IgM-specific peroxidase-conjugated probes. After washing, the plates can be developed with ABTS substrate (1 mg/ml) and analyzed at OD of 405-650. Alternatively, the IsoStrip Mouse Monoclonal Antibody Isotyping Kit (Roche, Cat. No. 1493027) may be used as described by the manufacturer.

C. Immunoconjugates

In another aspect, an anti-LLT1 antibody can be conjugated to a therapeutic moiety or agent, such as a cytotoxin, a drug (e.g., an immunosuppressant) or a radioisotope. Such conjugates are referred to herein as "immunoconjugates." Immunoconjugates which include one or more cytotoxins are referred to as "immunotoxins." A cytotoxin or cytotoxic agent includes any agent that is detrimental to and, in particular, kills cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Suitable therapeutic agents for forming immunoconjugates of the invention include, but are not limited to, antimetabolites (e.g., methotrexate, 6-mercaptopurine, 6-thioguanine, cytarabine, fludarabin, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC), and anti-mitotic agents (e.g., vincristine and vinblastine). In a preferred embodiment, the therapeutic agent is a cytotoxic agent or a radiotoxic agent. In another embodiment, the therapeutic agent is an immunosuppressant. In yet another embodiment, the therapeutic agent is GM-CSF. In a preferred embodiment, the therapeutic agent is doxorubicin, cisplatin, bleomycin, sulfate, carmustine, chlorambucil, cyclophosphamide or ricin A.

Antibodies of the present invention also can be conjugated to a radioisotope, e.g., iodine-131, yttrium-90 or indium-111, to generate cytotoxic radiopharmaceuticals for treating cancer. The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *pseudomonas* exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

D. Pharmaceutical Compositions

In another aspect, the present invention provides a composition, e.g., a pharmaceutical composition, containing one or a combination of antibodies of the present invention. The pharmaceutical compositions may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995. In one embodiment, the compositions include a combination of multiple (e.g., two or more) isolated antibodies of the invention which act by different mechanisms, e.g., one antibody which predominately acts by inducing CDC in combination with another antibody which predominately acts by inducing apoptosis.

Pharmaceutical compositions of the invention also can be administered in combination therapy, i.e., combined with other agents. For example, the combination therapy can include a composition of the present invention with at least one anti-inflammatory agent or at least one immunosuppressive agent. In one embodiment such therapeutic agents include one or more anti-inflammatory agents, such as a steroidal drug or a NSAID (nonsteroidal anti-inflammatory drug). Preferred agents include, for example, aspirin and other salicylates, Cox-2 inhibitors, such as rofecoxib (Vioxx) and celecoxib (Celebrex), NSAIDs such as ibuprofen (Motrin, Advil), fenoprofen (Nalfon), naproxen (Naprosyn), sulindac (Clinoril), diclofenac (Voltaren), piroxicam (Feldene), ketoprofen (Orudis), diflunisal (Dolobid), nabumetone (Relafen), etodolac (Lodine), oxaprozin (Daypro), and indomethacin (Indocin).

In another embodiment, such therapeutic agents include agents leading to the depletion or functional inactivation of regulatory T cells like low dose cyclophosphamid, anti-CTLA4 antibodies, anti-IL2 or anti-IL2-receptor antibodies.

In yet another embodiment, such therapeutic agents include one or more chemotherapeutics, such as Taxol derivatives, taxotere, gemcitabin, 5-Fluoruracil, doxorubicin (Adriamycin), cisplatin (Platinol), cyclophosphamide (Cytoxan, Procytox, Neosar). In another embodiment, antibodies of the present invention may be administered in combination with chemotherapeutic agents, which preferably show therapeutic efficacy in patients suffering from breast, lung, gastric, prostate, and/or ovarian cancer, or other cancer types.

In yet another embodiment, the antibodies of the invention may be administered in conjunction with radiotherapy and/or autologous peripheral stem cell or bone marrow transplantation.

In still another embodiment, the antibodies of the invention may be administered in combination with one or more antibodies selected from anti-CD25 antibodies, anti-EP-CAM antibodies, anti-EGFR, anti-Her2/neu, and anti-CD40 antibodies.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, e.g., antibody, bispecific and multispecific molecule, may be coated in a material to protect the compound from the action of acids and other natural conditions that may inactivate the compound.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Methods for the preparation of such formulations are generally known to those skilled in the art. See, e.g., Sustained and Controlled Release Drug Delivery Systems, J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al. (1984) *J. Neuroimmunol.* 7: 27).

Pharmaceutically acceptable carriers include sterile aqueous solutions or dispersions and sterile powders for the extemporaneous preparation of sterile injectable solutions or dispersions. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, niicroemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration.

Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a composition of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

In one embodiment, the antibodies of the invention may be administered by infusion, preferably slow continuous infusion over a long period, such as more than 24 hours, in order to reduce toxic side effects. The administration may also be performed by continuous infusion over a period of from 2 to 24 hours, such as from 2 to 12 hours. Such regimen may be repeated one or more times as necessary, for example, after 6 months or 12 months.

In yet another embodiment, the antibodies are administered by maintenance therapy, such as, e.g., once a week for a period of 6 months or more.

E. Diagnostic Methods

The monoclonal antibodies, or binding fragments thereof, according to the present invention, may be used to quantitatively or qualitatively detect the presence of LLT1 on cancer cells. This can be achieved, for example, by immunofluorescence techniques employing a fluorescently labeled antibody, coupled with light microscopic, flow cytometric, or fluorometric detection. In addition, the antibodies, or binding fragments thereof, according to the present invention may additionally be employed histologically, as in immunofluorescence, immunoelectron microscopy, or non-immuno assays, for in situ detection of the cancer-specific antigen on cells, such as for use in monitoring, diagnosing, or detection assays.

In situ detection may be accomplished by removing a histological specimen from a patient, and applying thereto a labeled antibody according to this invention. The antibody, or antigen-binding fragment thereof, is preferably applied by overlaying the labeled antibody or fragment onto the biological sample. Through the use of such a procedure, it is possible to determine not only the presence of the antigen, or conserved variants, or peptide fragments, but also its distribution in the examined tissue. One of ordinary skill in the art will readily recognize that any of a wide variety of histological methods, e.g., staining procedures, can be modified in order to achieve such in situ detection.

Immunoassay and other assays for the antigen (i.e., LLT1), or conserved variants, or peptide fragments thereof, typically comprise incubating a sample, such as a biological fluid, tissue extract, freshly harvested cells, or lysates of cells that have been incubated in cell culture, in the presence of a detectably-labeled antibody that recognizes the antigen, conserved variants, or peptide fragments thereof, such as the cancer-specific monoclonal antibodies, or binding fragments thereof, of the present invention. Thereafter, the bound antibody, or binding fragment thereof, is detected by a number of techniques well known in the art.

The biological sample may be brought into contact with, and immobilized onto, a solid phase support or carrier, such as nitrocellulose, or other solid support or matrix, which is capable of immobilizing cells, cell particles, membranes, or soluble proteins. The support may then be washed with suitable buffers, followed by treatment with the detectably-labeled antibody. The solid phase support may then be washed with buffer a second time to remove unbound antibody. The amount of bound label on the solid support may then be detected by conventional means. Accordingly, in another embodiment of the present invention, compositions are provided comprising the monoclonal antibodies, or binding fragments thereof, bound to a solid phase support, such as described herein.

By solid phase support or carrier or matrix is meant any support capable of binding an antigen or an antibody. Well-known supports or carriers include glass, plastic, nylon wool, polystyrene, polyethylene, polypropylene, dextran, nylon, amylases, films, resins, natural and modified celluloses, polyacrylamides, agarose, alumina gels, gabbros, and magnetite. The nature of the carrier can be either soluble to some extent, or insoluble for the purposes of the present invention. The support material may have virtually any possible structural configuration as long as the coupled molecule is capable of binding to an antigen or antibody. Thus, the support configuration may be spherical, as in a bead, cylindrical, as in the inside surface of a test tube, or the external surface of a rod. Alternatively, the surface may be flat, such as a sheet, film, test strip, stick, and the like. In addition, the solid support is preferably inert to the reaction conditions for binding and may have reactive groups, or activated groups, in order to attach the monoclonal antibody, a binding fragment, or the binding partner of the antibody. The solid phase support may also be useful as a chromatographic support, such as the carbohydrate polymers Sepharose, Sephadex, or agarose. Indeed, a large number of such supports for binding antibody or antigen are commercially available and known to those having skill in the art.

The binding activity for a given antibody may be determined by well-known methods. Those skilled in the art will be able to determine operative and optimal assay conditions for each determination by employing routine experimentation.

With respect to the anti-cancer antibodies, numerous ways to detectably label such protein molecules are known and practiced in the art. For example, one way the antibodies can be detectably labeled is by linking the antibody to an enzyme, e.g., for use in an enzyme immunoassay (EIA), (Voller et al., 1978, "The Enzyme Linked Immunosorbent Assay (ELISA)", Diagnostic Horizons, 2:1-7; Microbiological Associates Quarterly Publication, Walkersville, Md.; Voller et al., 1978, J. Clin. Pathol., 31:507-520; Butler et al., 1981, Meths. Enzymol., 73:482-523; Enzyme Immunoassay, 1980, (Ed.) Maggio, CRC Press, Boca Raton, Fla.; Enzyme Immunoassay, 1981, (Eds.) E. Ishikawa et al., Kgaku Shoin, Tokyo, Japan). The enzyme that is bound to the antibody reacts with an appropriate substrate, preferably a chromogenic substrate, so as to produce a chemical moiety which can be detected, for example, by spectrophotometric, fluorometric, or by visual detection means. Nonlimiting examples of enzymes which can be used to detectably label the antibodies include malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, ribonuclease, urease, catalase, glucose-6-phosphate dehydrogenase, glucoamylase and acetylcholinesterase. The detection can be accomplished by chrometric methods, which employ a chromogenic substrate for the enzyme, or by visual comparison of the extent of enzymatic reaction of a substrate compared with similarly prepared standards or controls.

A variety of other immunoassays may also be used for detection. For example, by labeling the antibodies, or binding fragments thereof, with a radioisotope, a radioimmunoassay (RIA) can be used to detect cancer-specific antigens (e.g., Colcher et al., 1981, Cancer Research, 41, 1451-1459; Weintraub, "Principles of Radioimmunoassays", Seventh Training Course on Radioligand Techniques, The Endocrine Society, March, 1986). The radioactive isotope label can be detected by using a gamma counter or a scintillation counter or by radiography.

The antibodies, or their antigen-binding fragments can also be labeled using a fluorescent compound. When the fluorescently labeled antibody is exposed to light of the proper wavelength, its presence can then be detected due to fluorescence. Some of the most commonly used fluorescent labeling compounds include fluorescein isothiocyanate, rhodamine, phycoerythrin, phycocyanin, allophycocyanin, o-phthaldehyde and fluorescamine. Detectably labeled fluorescence-emitting metals, such as 152Eu, or others of the lanthanide series, can be used to label the antibodies, or their binding fragments, for subsequent detection. The metals can be coupled to the antibodies via such metal chelating groups as diethylenetriaminepentacetic acid (DTPA), or ethylenediaminetetraacetic acid (EDTA).

The antibodies can also be detectably labeled by coupling them to a chemiluminescent compound. The presence of the chemiluminescent-tagged antibody is then determined by detecting the presence of luminescence that develops during the course of a chemical reaction. Examples of particularly useful chemiluminescent labeling compounds include, without limitation, luminol, isoluminol, theromatic acridinium ester, imidazole, acridinium salt and oxalate ester. Similarly, a bioluminescent compound may be used to label the antibodies of the present invention. Bioluminescence is a type of chemiluminescence found in biological systems in which a catalytic protein increases the efficiency of the chemiluminescent reaction. The presence of a bioluminescent protein is determined by detecting the presence of luminescence. Useful bioluminescent labeling compounds include luciferin, luciferase and aequorin.

Another embodiment of the present invention provides diagnostics, diagnostic methods and imaging methods for cancers and tumors using the monoclonal antibodies and binding fragments thereof as described by the present invention. The diagnostic uses of the antibodies according to the present invention embrace primary tumors and cancers, as well as metastases. Other cancers and tumors bearing the antigen are also amenable to these diagnostic and imaging procedures.

A diagnostic method according to the invention comprises administering, introducing, or infusing the monoclonal antibodies or their binding fragments as described herein, with or without conjugation to a detectable moiety, such as a radioisotope. After administration or infusion, the antibody or binding fragment binds to the tumor or cancer cells, after which the location of the bound antibodies or fragments is detected. For detectably labeled antibodies or fragments, for example, those labeled with a radioisotope, imaging instrumentation may be used to identify the location of the agent within the body. For unlabeled antibodies or fragments, a second detectable reagent may be administered, which locates the bound antibodies or fragments so that they can be suitable detected. Similar methods have been employed for other antibodies, and the skilled practitioner will be aware of the various methods suitable for imaging the location of detectably bound antibodies or fragments within the body. As a general guidance, about 10-1000 μg, preferably about 50-500 μg, more preferably about 100-300 μg, most preferably about 200-300 μg of Protein G-purified mAb are administered. For mice, for example, using 200 μg mAb and intraperitoneal (i.p.) administration, mAb is injected three times a week for three weeks. For 300 μg mAb and intraperitoneal (i.p.) administration, mAb is injected two times a week for three weeks. Applicable doses for humans include about 100-200 mcg/kg, or 350-700 mg/m2.

In a related embodiment, the present invention provides methods for diagnosing cancers by assaying for changes of levels in the cancer-specific antigen in cells, tissues or body fluids compared with the levels in cells, tissues, or body fluids, preferably of the same type, from normal human controls. A change, especially an increase, in levels of antigen (i.e., LLT1) in the patient versus the normal human control is associated with the presence of cancer. Typically, for a quantitative diagnostic assay, a positive result indicating that the patient being tested has cancer, is one in which levels of the antigen in or on cells, tissues or body fluid are at least two times higher, and preferably three to five times higher, or greater, than the levels of the antigens in or on the same cells, tissues, or body fluid of the normal individual as control. Normal controls include a human without cancer and/or non-cancerous samples from the patient.

EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Overexpression of LLT1 (OCIL, CLEC2D) on Prostate Cancer Cells Inhibits NK Cell-Mediated Killing Through LLT1-NKRP1A (CD161) Interaction A. Results Human Prostate Cancer Cells Express LLT1.

LLT1 has been reported to be expressed on activated lymphocytes (NK, T and B cells) and antigen-presenting cells i.e. macrophages and dendritic cells. Also, human malignant glioma cells showed high expression of LLT1 and their expression increased with the WHO grade of malignancy[30]. qRT-PCR analysis of four prostate cancer cell lines (PC3, DU145, LNCaP and 22Rv1), a normal prostate cell line (PWR-1E) showed increased expression of LLT1 at the mRNA level. 22Rv1 showed significantly high expression of LLT1 (***, $p<0.001$) (FIG. 1A). The western blot analysis confirmed qRT-PCR results showing increased expression of LLT1 on all four prostate cancer cell lines. Surprisingly, the normal prostate cells PWR-1E also showed high expression of LLT1 (FIG. 1B and FIG. 1C).

Prostate Cancer Cells Display Increased Cell Surface Expression of LLT1.

Figure 3:
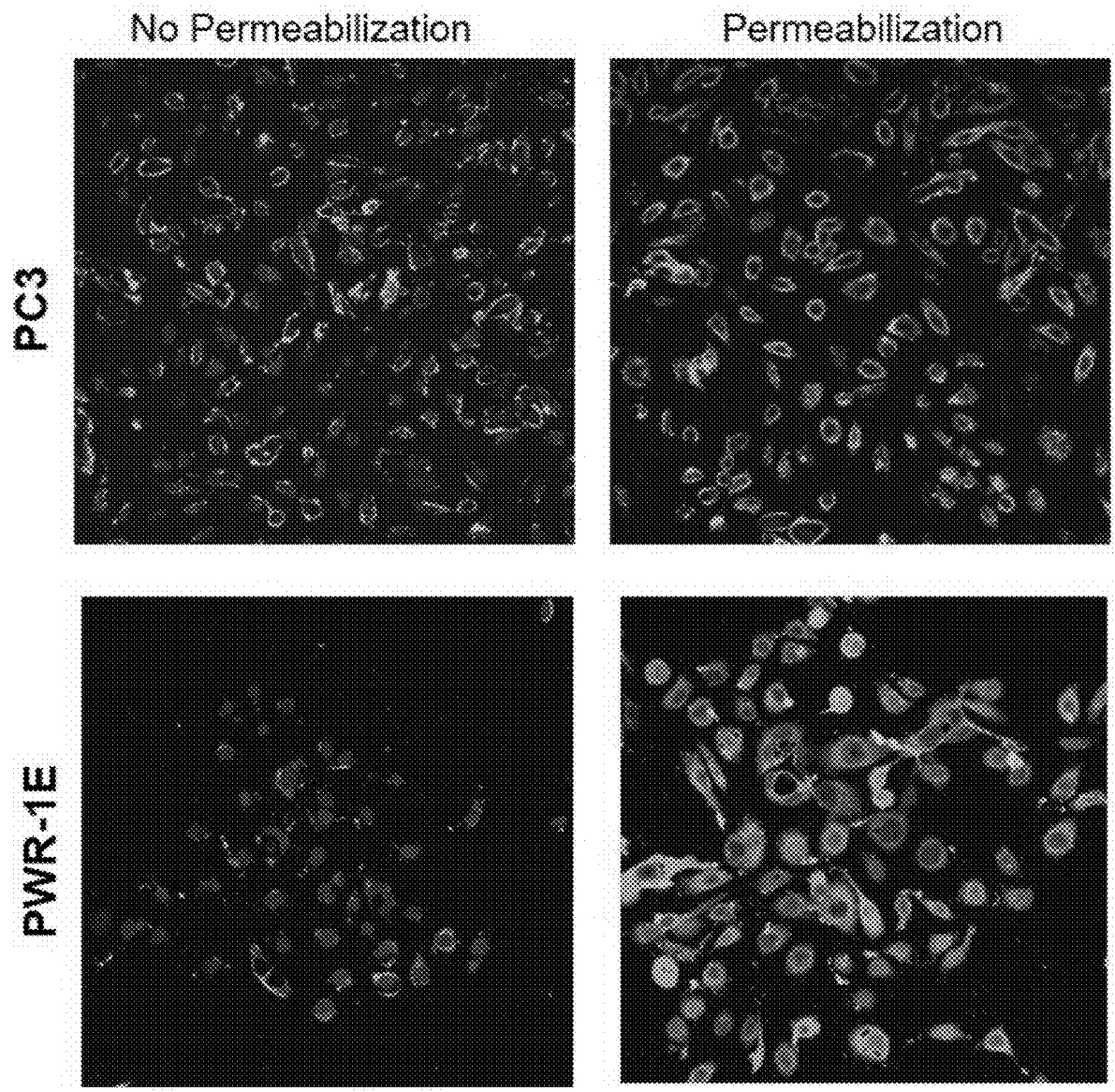
FIG. 3. Prostate cancer cells overexpress LLT1 on the cell surface as compared to intracellular LLT1 expression in normal prostate cells. Normal prostate cells, PWR-1E and metastatic prostate cancer cells, PC3 were fixed, blocked, and incubated with mouse anti-human LLT1 antibody with or without permeabilization, followed by anti-mouse Alexa 488 secondary antibody (green). DNA was counterstained with DAPI (blue). The slides were examined using LSM 510 Meta confocal microscope system.

Flow cytometry analysis revealed cell surface expression of LLT1 on all the four prostate cancer cell lines DU145, LNCaP, PC3 and 22Rv1 cells (FIG. 2). Increased surface expression of LLT1 was observed on DU145 cells (MFIR—12) and 22Rv1 (MFIR—14.45) as compared to other prostate cancer cells (FIG. 2). In contrast to the qRT-PCR and western blot analysis there was very minimal to no expression of LLT1 on PWR-1E (normal prostate cell line) and Jurkat (acute T cell leukemia) cells (FIG. 2E to FIG. 2F). Due to the contradictory results of the qRT-PCR, western blot analysis and flow cytometry results with PWR-1E (normal prostate cells) the inventors performed immunofluorescence staining with or without permeabilization and analyzed by confocal microscopy. Interestingly, PWR-1E cells showed abundant expression of LLT1 intracellularly but very minimal to no expression on the cell surface. In contrast, PC3 cells showed increased LLT1 expression both intracellularly as well as on the cell surface (FIG. 3). These results suggest that overexpression of LLT1 on the cell surface of prostate cancer cells could play a role in its escape from immune attack.

Prostate Cancer Tissues Showed Increased Expression of LLT1 as Compared to Normal Prostate Tissues.

Prostate cancer and normal prostate tissues were obtained from National Disease Research Interchange (NDRI). H & E staining of prostate cancer tissues revealed several infiltrating lymphocytes (shown by arrows) as compared to normal prostate tissue (FIG. 4C and FIG. 4D). Furthermore, when the tissues were stained with LLT1 Ab (mouse anti-human CLEC2D Ab, Lifespan Biosciences, Seattle, Wash.) and counter stained with anti-Mouse-IgG-Dylight 594 Ab, prostate cancer tissues showed high expression of LLT1 (shown by the red/pink stain) as compared to normal prostate tissues that showed very minimal expression of LLT1 confirming the findings that were obtained in prostate cancer cell lines (FIG. 5C and FIG. 5D).

Blocking LLT1 on Prostate Cancer Cells Enhances NK Cell-Mediated Lysis of Prostate Cancer Cells.

To assess the functional role of LLT1 on prostate cancer cells, cell surface expression of LLT1 on PC3, DU145, LNCaP, 22Rv1, PWR-1E and Jurkat cells was blocked with an anti-human LLT1 mAb and subsequently labeled with radioactive $^{51}Cr$. The cells were then incubated with primary NK cells from healthy individuals and the cytolytic activity was determined by the chromium release assay at effector to target (E:T) ratios of 25:1, 5:1 and 1:1. Primary NK cells incubated with PC3, DU145, LNCaP and 22Rv1 cells blocked with mouse anti-human LLT1 mAb (LLT1) showed significantly higher NK cell mediated cytolytic activity as compared to the cells incubated with mouse IgG1 isotype control antibody (cAb) (FIG. 6). However, PWR-1E normal prostate cells and Jurkat cells (data not shown) blocked with LLT1 mAb did not show any significant difference in NK cell-mediated cytolytic activity as compared to cells incubated with isotype control antibody (cAb). Moreover, the cytolytic activity of NK cells against normal prostate cells were much lower than all the prostate cancer cells. This suggests that the interaction of LLT1 on the cell surface of prostate cancer cells with NKRP1A on NK cells inhibits the cytolytic activity of NK cells against prostate cancer cells supporting the immune evasion by prostate cancer cells.

LLT1 is Expressed on Breast Cancer Cells and Inhibit NK Mediated Killing.

Figure 7A:
FIGS. 7A-C. LLT1 is expressed on breast cancer cells and inhibit NK mediated killing. (A) RT-PCR amplification of LLT1 mRNA from breast cancer cells, SKBR3, MDA231 and MCF7; (B) FACS analysis of LLT1 expression on MCF7 breast cancer cells: Histogram—anti-human LLT1 with PE conjugated secondary anti-mouse IgG1; Clear Histogram—PE conjugated anti-mouse secondary antibody only; (C) Blocking of LLT1 with anti-LLT1 mAb increased killing of MCF7 cells by freshly isolated human NK cells.
Figure 7B:
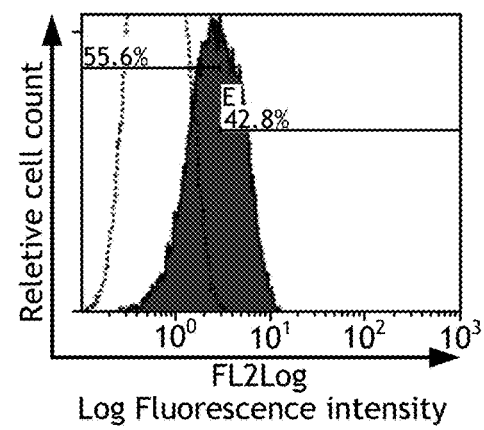
Figure 7C:
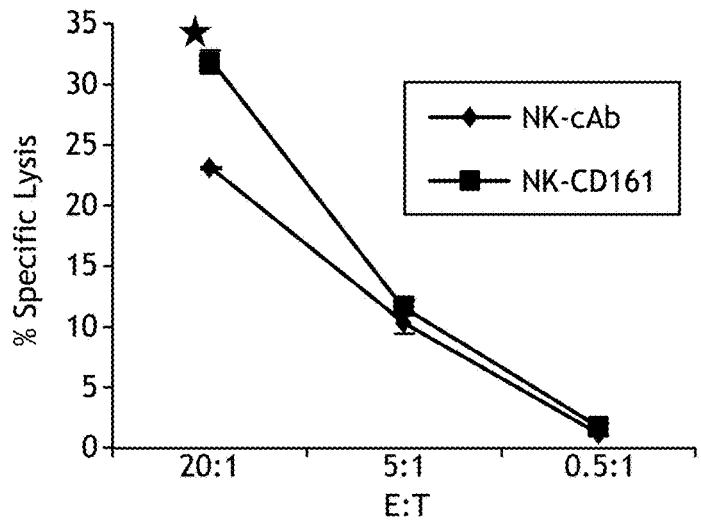
Figure 8A:
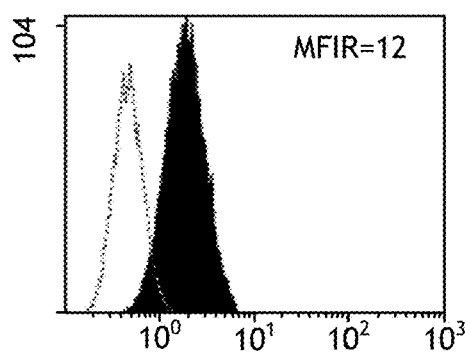
FIGS. 8A-B. Flow cytometry analysis demonstrating inhibition of cell surface expression of LLT1 on Prostate Cancer cells DU145 by LLT1 specific siRNA. (A) LLT1 expression on DU145 cells without siRNA treatment. Surface expression of LLT1 on DU145 cells was determined by flow cytometry using mouse anti-human LLT1 mAb (clone #2E5) and a PE conjugated goat anti-mouse IgG polyclonal secondary antibody. (B) LLT1 expression on DU145 cells after siRNA treatment. All DU145 samples were analyzed by flow cytometry analysis 96 hours after transfection. Dotted histogram represents isotype control (mIgG1-PE mAb) staining and filled histogram shows LLT1 expression. MFIR is the mean fluorescence intensity ratio.
Figure 8B:
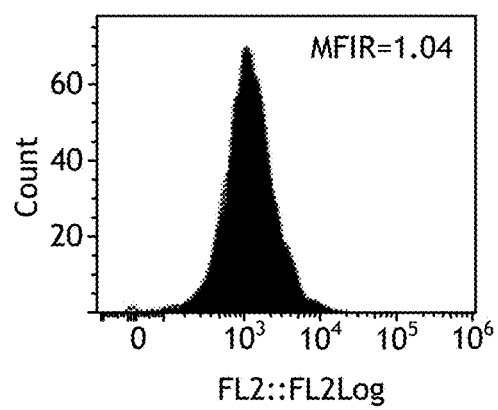
Figure 11:
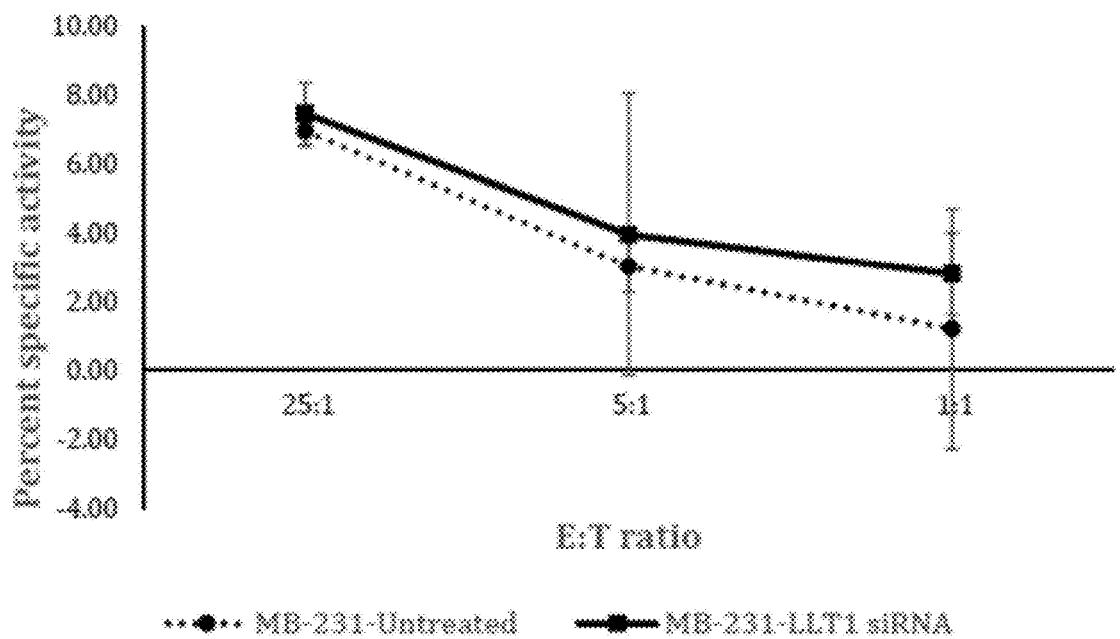
FIG. 11. Increased killing of LLT1 specific siRNA treated MDA-MB 231 cells by NK cells. The cell surface expression of LLT1 on MDA-MB 231 cells was downregulated by siRNA treatment and subsequently labeled with radioactive $^{51}$Cr. The labeled cells were incubated with primary NK cells from a healthy individual and the cytolytic activity was determined by the standard 4 hr radioactive $^{51}$Cr release assay at an Effector to target (E:T) ratios of 25:1, 5:1 and 1:1. Assays were performed in triplicates and the error bars refer to the means SD generated from the triplicates. Student's t-test was used to compare cytotoxicity of primary NK cells against untreated MDA-MB 231 cells and the LLT1 siRNA treated MDA-MB 231. (*, $p<0.05$; **, $p<0.005$).
Figure 12:
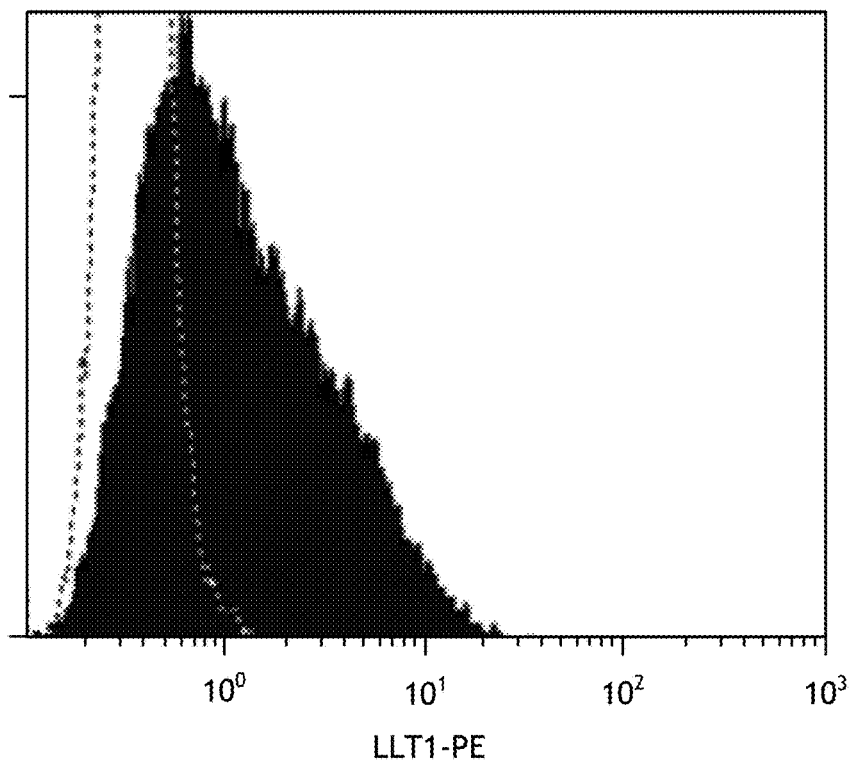
FIG. 12. LLT1 transfected K562 cells binding to LLT1 mAb clone 2E5. LLT1 transfected K562 with isotype IgG1 (empty), LLT1 transfected K562 with LLT1 mAb clone 2E5 (filled).
Figure 13:
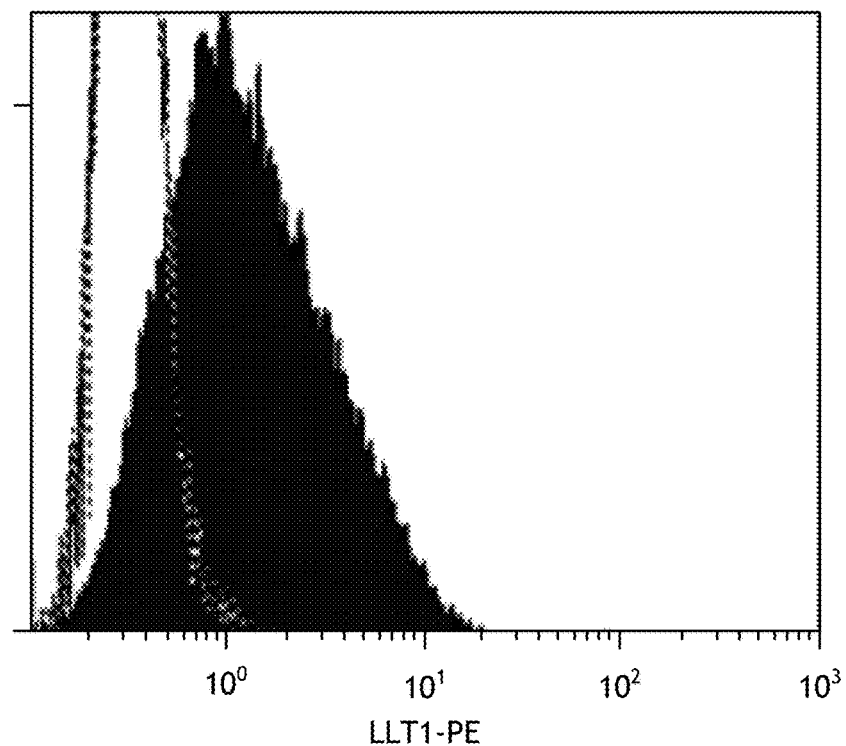
FIG. 13. LLT1 transfected K562 cells binding to LLT1 mAb clone 3G1. LLT1 transfected K562 with isotype IgG2a (empty), LLT1 transfected K562 with LLT1 mAb clone 3G1 (filled).
Figure 14:
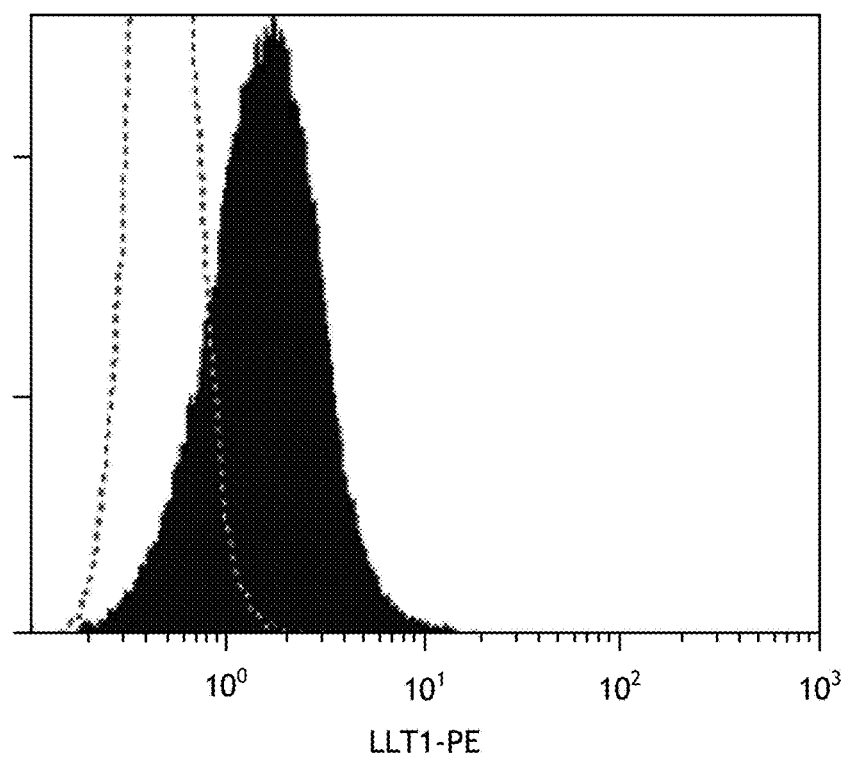
FIG. 14. Prostate cancer cells DU145 binding to LLT1 mAb clone 2E5. Prostate cancer cells DU145 with isotype IgG1 (empty), Prostate cancer cells DU1.45 with LLT1 mAb clone 2E5 (filled).
Figure 15:
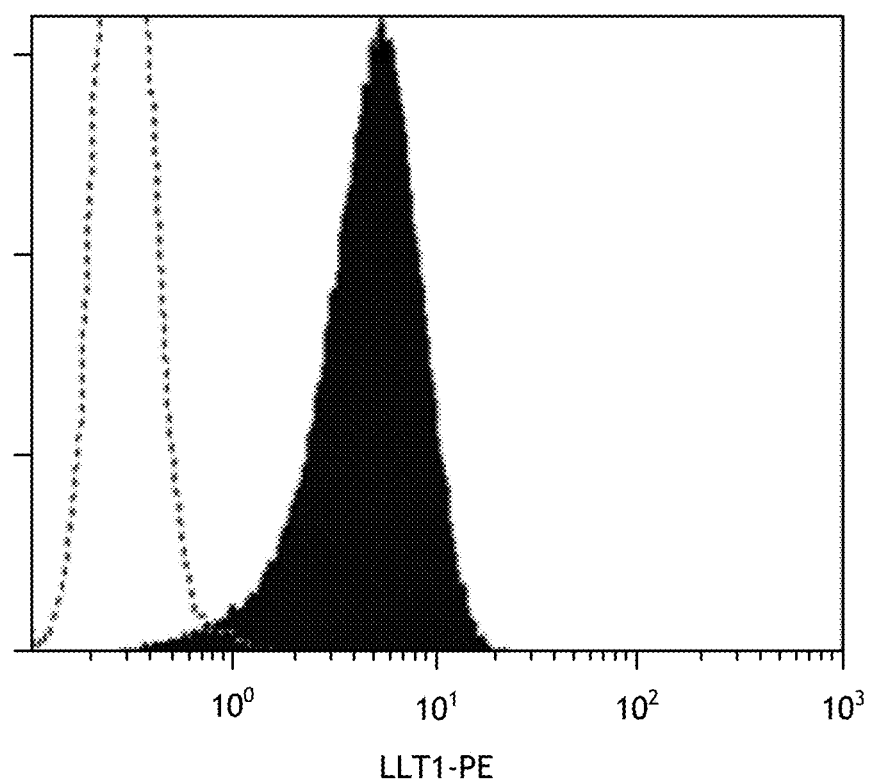
FIG. 15. Prostate cancer cells DU145 binding to LLT1 mAb clone 3G1. Prostate cancer cells DU145 with isotype IgG2a (empty), Prostate cancer cells DU145 with LLT1 mAb clone 3G1 (filled).

The inventors also examined the expression of LLT1 on several breast cancer cells. It was found that LLT1 is expressed on all three breast cancer cells (MCF7, MDA231 and SKBR3) examined. The results showed that LLT1 mRNA and protein are expressed in MCF7, MDA231 and SKBR3 breast cancer cells (FIG. 7). Blocking of LLT1-CD161 interaction with anti-LLT1 mAb increased the killing of MCF7 cells (FIG. 7).

Triple-Negative Breast Cancer (TNBC) Cells Express LLT1.

Expression of LLT1 at the cell surface of TNBC cells were identified through flow cytometry analysis. Non-tumorigenic breast cell line MCF10A and TNBC cell lines MDA-MB-231 and MDA-MB-436 were treated with human Fc fragment, then were subsequently stained with either anti-anti-human LLT1-PE antibodies or isotype control IgG1-PE antibodies. Two TNBC cell lines' cell surface LLT1 expression was compared to non-tumorigenic breast cell line MCF10A to determine if there is greater LLT1 expression on TNBCs than normal breast cells. One representative TNBC cell line MDA-MB-231 displayed the highest cell surface expression of LLT1 at median fluorescence intensity ratio (MFIR) of 1.84 with 13.3 percent of cells positive for cell surface LLT1 expression (FIG. 16A). TNBC cell line MDA-MB-436 also displayed cell surface expression of LLT1 at MFIR of 1.36 with 4.4 percent of cells positive for LLT1 (FIG. 16A). Both TNBC cell lines had significantly higher expression of LLT1 based on MFIR and percent of cells positive for LLT1 compared to normal breast cell line MCF10A.

To confirm consistency in detecting cell surface LLT1 expression, 3 independent experiments of flow cytometry analysis were performed for each cell line tested (FIG. 16B). MFIRs and percentage of cells that were positive for LLT1 expression from these 3 independent experiments were averaged. Both TNBC cell lines, MDA-MB-231 and MDA-MB-436 had significantly greater expression of cell surface LLT1 than normal breast cell line MCF10A (FIG. 16B). MDA-MB-231 mean of MFIRs of 1.80 and its mean percent LLT1+ cells of 14.67% was statistically significantly higher (Mean of MFIRs and % LLT1+** $p<0.01$, FIG. 16B) than non-tumorigenic breast cell line MCF10A's respective values of 0.95 and 0.56% LLT1+ cells. MDA-MB-436 showed a higher expression of LLT1 based on mean of MFIRs of 1.34 and mean percent LLT1+ cells of 6.54% than MCF10A, but still much lower than MDA-MB-231 respective values. Hence, flow cytometry analysis under the same culture conditions and stained with the same anti-LLT1-PE antibodies consistently showed that TNBCs show higher cell surface expression of LLT1 than non-tumorigenic breast cell line MCF10A. These results demonstrate that LLT1 may serve as a possible target of interest.

Figure 17:
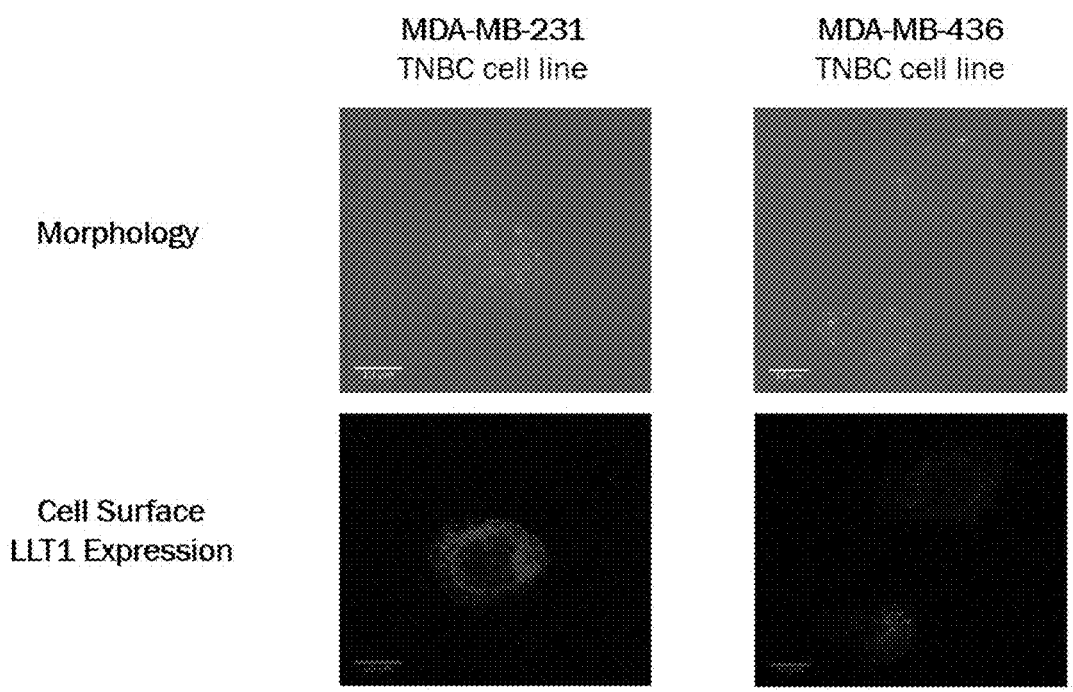
FIG. 17. Triple-negative breast cancer cells expressed LLT1 at the cell surface. Triple-negative breast cancer cells MDA-MB-231 and MDA-MB-436 were fixed, blocked with human Fc fragment, and stained with anti-human LLT1-PE antibody. The cells were examined with a Zeiss LSM 510 Confocal Laster Microscope at 40× objective. Scale bar is 10 μm.

To further confirm expression of LLT1 on TNBCs, immunofluorescent staining on TNBC cell lines MDA-MB-231 and MDA-MB-436 were performed. Both TNBCs were treated with human Fc fragment and then were stained with anti-human LLT1-PE antibodies. MDA-MB-231 also showed higher expression of LLT1 at the cell surface than MDA-MB-436 (FIG. 17). These results suggest that expression of LLT1 as an inhibitory ligand on TNBCs could play a role in the TNBC cells evading NK cell-mediated lysis. Expression of LLT1 on TNBCs shown by both flow cytometry analysis and immunofluorescent staining leads to LLT1 as a target of interest in blocking LLT1-NKRP1A interaction between TNBCs and primary NK cells.

Blocking LLT1 with Antibodies at the Cell Surface of TNBCs Increased NK Cell-Mediated Lysis Against these Tumor Cells.

To assess the function of LLT1, TNBC cell lines MDA-MB-231 and MDA-MB-436 and non-tumorigenic cell line MCF10A were radiolabeled with $^{51}Cr$ and treated with anti-human LLT1 antibodies or isotype IgG antibodies. The labeled cells blocked with its antibodies were co-incubated with primary NK cells for 3.5 hours at effector-to-target ratios (E:T) of 25:1, 5:1, and 1:1. Cytolytic activity, percent of cells lysed by primary NK cells, were subsequently quantified. Primary NK cells isolated from peripheral blood mononuclear cells derived from whole blood, were used. Fc receptors on primary NK cells were blocked with human Fc fragment to prevent antibody-dependent cell-mediated cytotoxicity (ADCC) from occurring.

Figure 18:
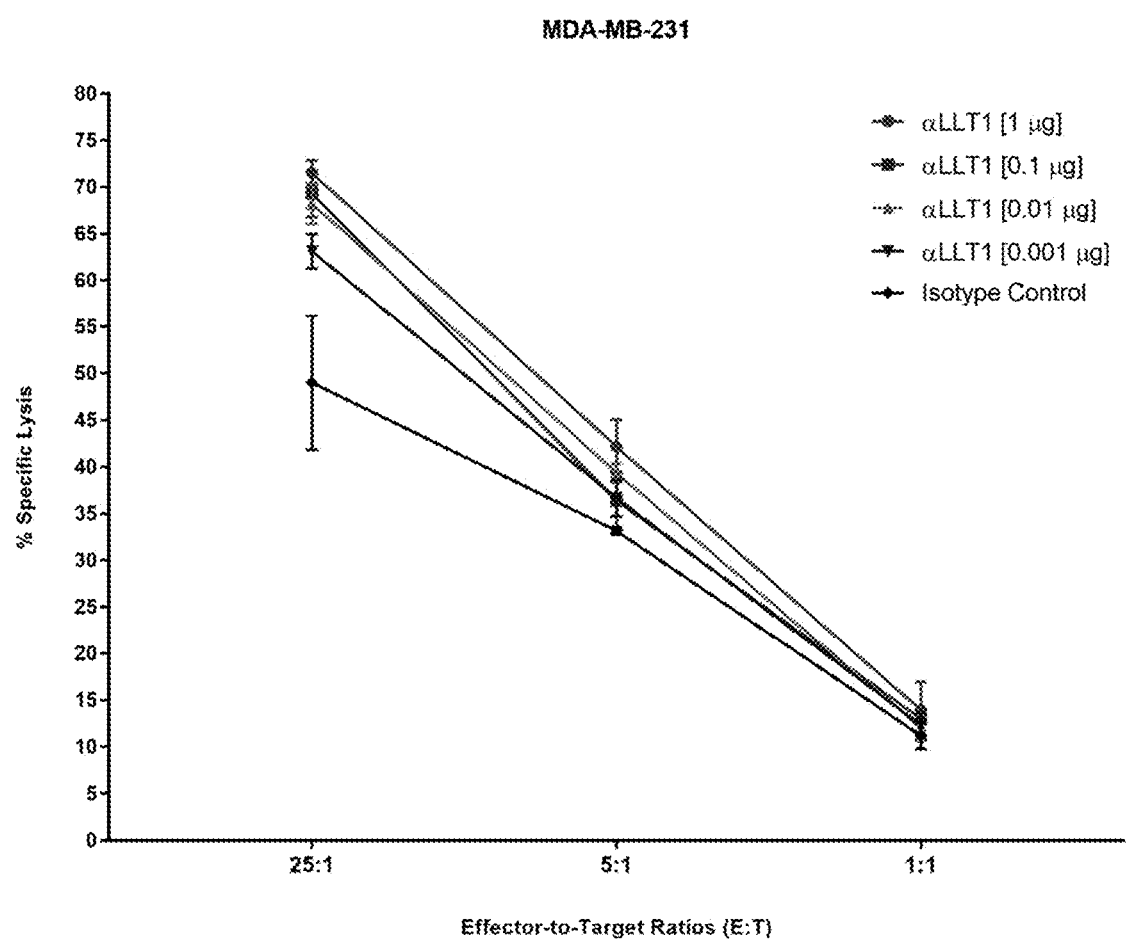
FIG. 18. Anti-LLT1 antibody dose-dependent treatment on TNBC MDA-MB-231 demonstrates enhanced killing by primary NK cells. TNBC cell line MDA-MB-231 was treated with either anti-human LLT1 antibodies (αLLT1) or isotype control antibodies. MDA-MB-231 cells were treated with anti-LLT1 antibodies at four different concentrations. There is greatest lysis of TNBCs when treated with anti-LLT1 antibodies at 1 μg per well compared to other concentrations and isotype IgG control (p=0.08, student paired t-test). Cells were labeled with $^{51}$Cr and then were co-incubated with primary NK cells isolated from PBMCs derived from whole blood of healthy volunteers at effector-to-target ratios (NK-to-5000 TNBCs) of 25:1, 5:1, and 1:1 for 3.5 hours. Specific lysis of labeled cells was subsequently quantified and calculated. This assay was performed in triplicates and error bars indicate standard deviations.

Treatment of TNBC cell lines MDA-MB-231 with anti-LLT1 antibodies was performed at four concentrations to determine concentration of antibody to use for targeting LLT1 on TNBCs (FIG. 18). Based on the effects of lysis based on the different concentrations of anti-LLT1 antibody, LLT1 on TNBC cell lines was targeted by treatment with 1 µg of anti-LLT1 antibody (FIG. 19). Blocking LLT1 on both TNBCs MDA-MB-231 and MDA-MB-436 enhanced specific lysis by NK cells (FIG. 19B and FIG. 19C). MDA-MB-231 and MDA-MB-436 had increased specific lysis by NK cells when LLT1 was blocked than cells treated with isotype IgG antibodies.

At 25:1 E:T ratio, there was a statistically significant difference in percent specific lysis of MDA-MB-231 cells between cells treated with anti-LLT1 antibodies compared to cells treated with IgG isotype antibody (FIG. 19B). At 25:1 ratio, 19.71% of MDA-MB-231 treated with anti-LLT1 antibodies were killed by primary NK cells compared to 2.02% of MDA-MB-231 cells treated with IgG isotype antibody. There was a distinct difference between the percent specific lysis of MDA-MB-231 cells treated with anti-LLT1 antibodies compared to non-tumorigenic breast MCF10A cells treated with the same anti-LLT1 antibody at the 25:1 E:T ratio. At 25:1 ratio, 7.54% of MCF10A cells treated with anti-LLT1 antibody were killed by primary NK cells compared to 2.96% of MCF10A cells treated with IgG isotype antibody. At 5:1 E:T ratio, there was a statistically significant difference in percent specific lysis of MDA-MB-231 cells treated with anti-LLT1 antibodies compared to treatment with isotype antibodies.

Effects of blocking LLT1-NKRP1A interaction by treating TNBC cell line MDA-MB-436 with anti-LLT1 antibodies (FIG. 19C) were tested. Lower percentage of MDA-MB-436 cells were killed by NK cells than MDA-MB-231 cells at all the E:T ratios. The lower percentage of MDA-MB-436 cells killed can be attributed to the lower expression of cell surface LLT1 on this cell line in contrast to MDA-MB-231 LLT1 expression as shown in flow cytometry analysis. At 25:1 E:T ratio, 8.39% of MDA-MB-436 cells treated with anti-LLT1 antibodies were killed while 4.75% of cells treated with isotype antibodies were killed.

Treating MDA-MB-231 and MDA-MB-436 cells with anti-LLT1 antibodies allowed an increase of killing by primary NK cells. Furthermore, MDA-MB-231 cells treated with anti-LLT1 antibodies had a greater percent of cells killed compared to non-tumorigenic breast cell line MCF10A treated with anti-LLT1 antibodies. The greater percentage of MDA-MB-231 cells killed when targeting LLT1 with antibodies than MCF10A cells was consistent with flow cytometry analysis demonstrating that MDA-MB-231 cells had a statistically significant higher expression of cell surface LLT1 in contrast to LLT1 cell surface expression on MCF10A. The lower percent of MCF10A being killed when targeting LLT1 with anti-LLT1 antibodies supports that LLT1 may serve as a possible target that would favor killing TNBCs while minimizing killing healthy breast cells. Blocking LLT1 with antibodies on TNBC cells increases cytolytic targeting by primary NK cells. Hence, blocking LLT1 interaction with NK cell receptor NKRP1A suppresses inhibitory signal transduction in NK cells. These results suggest that the function of LLT1 on TNBC cells inhibits NK cell activation of cytolytic function against TNBCs expressing LLT1 due to the LLT1-NKRP1A interaction. Expression of LLT1 on triple-negative breast cancer cells serves a role in evading immunosurveillance by NK cells.

Gene Knockdown of LLT1 Downregulated Cell Surface Expression of LLT1 on TNBCs and Enhances NK Cell-Mediated Lysis of TNBCs.

To further assess the function of LLT1 as an inhibitory ligand on TNBC cells, gene knockdown of LLT1 on the MDA-MB-436 cell line to decrease the expression of LLT1 at the cell surface, was performed. TNBC MDA-MB-436 was transfected with lipid-mediated small interference RNAs (siRNA) that targets the LLT1 gene for 63 hours. As a negative control, TNBC cell line MDA-MB-436 was transfected with non-targeting siRNAs (scramble siRNA) which does not target the LLT1 gene. Knockdown of cell surface LLT1 was confirmed by flow cytometry analysis after 63 hours of transfection before testing the transfected cells for killing by primary NK cells. MDA-MB-436 LLT1 siRNA-transfected or scramble siRNA-transfected cells were blocked with human Fc fragment and stained with anti-human LLT1-PE antibodies. MDA-MB-436 cells transfected with LLT1 siRNA showed negligible expression of LLT1 at the cell surface (FIG. 20A, MFIR 0.31) versus MDA-MB-436 cells transfected with scramble siRNA (FIG. 20A, MFIR 1.09). After confirming decreased expression of LLT1 at the cell surface of MDA-MB-436, testing that knockdown of LLT1 enhances natural killer cell-mediated lysis of these transfected triple-negative breast cancer cells, was performed.

Upon confirmation of knockdown, to assess that knockdown of LLT1 increases killing of TNBC cells, MDA-MB-436 transfected with either LLT1 siRNA or scramble siRNA were labeled with $^{51}Cr$ and then were co-incubated with primary NK cells for 3.5 hours MDA-MB-436 with confirmed knockdown of LLT1 had a higher percent specific lysis at both 25:1 and 5:1 E:T ratios in contrast to its scramble siRNA transfected cells (FIG. 20B). At 25:1 E:T ratio, 63.38% of MDA-MB-436 LLT1 siRNA-transfected cells were killed by NK cells compared to 42.18% of MDA-MB-436 scramble siRNA-transfected cells killed (FIG. 20B, p=0.07 compared to scramble siRNA control). At 5:1 E:T ratio, 21.83% of MDA-MB-436 LLT1 siRNA-transfected were killed compared to 18.87% of scramble siRNA-transfected cells.

Hence, transfecting MDA-MB-436 cells with siRNA targeting the LLT1 gene decreases expression of LLT1 at the cell surface. Decreasing the expression of cell surface LLT1 prevents interaction of LLT1 with NKRP1A on primary NK cells. These results indicate that knockdown of LLT1 at the cell surface of TNBC cells enhances specific lysis by NK cells. Disrupting the LLT1-NKRP1A interaction prevents inhibitory signal transduction to NK cells thus favoring activation of natural killer cells to lyse these TNBC cells. These results further confirm that the function of LLT1 on the cell surface of TNBC cells allows evasion of immune system recognition and cytolytic targeting by NK cells.

B. Materials and Methods

Cell Culture and Reagents.

Human prostate cancer cell lines DU145 (ATCC HTB-81), LNCaP (ATCC CRL-1740), and PC3 (ATCC CRL-1435) are derived from metastatic prostate cancer samples, castrate resistant for PC3 and DU145; and castrate-sensitive for LNCaP. 22Rv1 (ATCC CRL-2505) is a human prostate carcinoma epithelial cell line derived from a xenograft that was serially propagated in mice after castration-induced regression and relapse of the parental, androgen-dependent CWR22 xenograft. PWR-1E (ATCC CRL-11611) are epithelial cells derived from the peripheral zone of a histologically normal adult human prostate. Jurkat is a human T acute lymphocytic leukemia cell (ATCC-TIB-152). DU145, LNCaP, 22Rv1 and Jurkat were cultured in 4+ RPMI complete medium (RPMI 1640 supplemented with 10% fetal bovine serum (FBS), 2 mM glutamine, 100 U/ml penicillin, 100 streptomycin, 10 mM HEPES, and 10 mM nonessential amino acids). PC3 cells were cultured in Dulbecco's modified Eagle's medium (DMEM, Gibco Life Technologies) supplemented with 10% FBS (Atlanta Biologicals, Lawrenceville, Ga.). PWR-1E cells were grown in a keratinocyte serum free medium (K-SFM) supplemented with 0.05 mg/ml BPE and 5 ng/ml EGF. Peripheral blood mononuclear cells (PBMCs) were isolated from ethylene-diamine-tetraacetic acid (EDTA)-treated whole-blood samples by Histopaque-1077 (Sigma Chemicals, St. Louis, Mo.) density gradient centrifugation using LeucoSep tubes (Greiner, Monroe, N.C.) from healthy individuals with prior approval from Institutional Review Board (IRB) of UNT Health Science Center, Fort Worth, Tex. Primary NK cells were isolated from the PBMCs using NK isolation kit (Miltenyi Biotec, San Diego, Calif.) and the purity was determined by flow cytometry using anti-human CD56 mAb.

Quantitative Reverse Transcriptase-Polymerase Chain Reaction (qRT-PCR) and Flow Cytometry Analysis.

Five million cells were dissolved with 1 ml of RNA STAT-60. RNA was extracted by chloroform and precipitated by isopropanol. After resuspension with 0.1% diethylpyrocarbonate (DSPC)-water, RNA purity and concentration was determined by measuring optical density. 2 µg of RNA was used for cDNA synthesis in the presence of random primer mix (NEB). After RT reaction, 100 ng of cDNA was used as a template and LLT1 specific primers were used to amplify LLT1 by quantitative PCR using Taqman gene expression assays in an Eppendorf Realplex2 Mastercycler. Reactions were done in 20 µl triplicates using the $\Delta\Delta CT$ method, with GAPDH as the reference gene. The results presented are an average of three independent experiments.

Surface expression of human LLT1 was detected using flow cytometry. All the cell lines were stained for LLT1 with mouse anti-human LLT1 mAb (clone #2E5 or 3G1) and a PE conjugated goat anti-mouse IgG polyclonal secondary antibody and an isotype control antibody (mIgG1-PE mAb) (R&D Systems, Minneapolis, Minn.) and subjected to flow cytometry analysis using the Beckman and Coulter Cytomics FC 500 Flow cytometer.

Preparation of Cell Extracts and Western Blot Analysis.

Cells were lysed in radioimmunoprecipitation assay (RIPA) lysis buffer (50 mM Tris-HCl, pH 7.5; 150 mM sodium chloride; 0.5% sodium deoxycholate; 1% Nonidet P-40; 0.1% sodium dodecyl sulfate), supplemented with protease and phosphatase inhibitor cocktail (Millipore, Billerica, Mass.), at 4° C. for 30 min. After sonication on ice, cell debris was removed by centrifugation at 12,000 g for 10 min at 4° C. Protein concentrations were determined by Pierce BCA protein assay kit (Thermo Scientific, Rockford, Ill.). Cell extracts were separated on 4-20% Bis-Tris Nu-PAGE gel (Life Technologies, NY) using MES buffer and transferred onto nitrocellulose membrane using an iBlot (Life Technologies, NY). Membranes were blocked with 5% fat-free milk in Tris-buffered saline containing 0.05% Tween 20 (TBST) at room temperature for 60 min, and incubated overnight at 4° C. with mouse anti-human LLT1 antibody in 5% milk in TBST. After three washings with TBST, the membrane was incubated with horseradish peroxidase (HRP)-linked anti-mouse secondary antibody (SouthernBiotech, Birmingham, Ala.) at room temperature for 2 hr. After washing again with TBST, the membranes were developed using ECL plus (Amersham Pharmacia. Biotech, IL), and the image was captured using alpha-imager Fluoretech HD2 (ProteinSimple, San Jose, Calif.). Bands were analyzed using the NIH ImageJ software [45].

Immunofluorescence Studies.

Cells were grown to 60 to 70% confluence on glass coverslips in 12-well plates. Cells were washed with ice-cold PBS, fixed with 4% paraformaldehyde for 30 min, and then permeabilized with 0.1% Triton X-100 for 20 min if required. The slides were then washed with PBS, incubated with 5% goat serum in PBS for 2 h, and then incubated with mouse anti-human LLT1 antibody, that was diluted 1:100 in PBS, overnight at 4° C. After washing with PBS three times, the coverslips were incubated with Alexa Fluor 488 goat anti-mouse IgG (Life Technologies, Eugene, Oreg.), that was diluted 1:400 in PBS, for 2 h at room temperature in darkness. The coverslips were then washed with PBS and mounted on glass slides with ProLong Gold anti-fade reagent containing DAPI (1.5 µg/ml) (Invitrogen Inc., Eugene, Oreg., USA). The slides were examined using LSM 510 Meta confocal system equipped with an inverted microscope (Axio Observer Z1, Carl Zeiss, Thornwood, N.Y.).

Prostate Cancer Tissues, H & E Staining and Immunohistochemistry.

Prostate cancer and normal prostate tissues were obtained from National Disease Research Interchange (NDRI). The prostate tissue specimens were obtained by radical prostatectomy with one of them displaying a histologic type of adenocarcinoma with focus of mucinous adenocarcinoma with a total gleason score of 7. The other prostate tissue specimen was an adenocarcinoma, with focal ductal features and total gleason score of 8. The de-identified paraffinized tissue blocks were sectioned by standard microtomy procedures using a Thermo Microm HM 355S microtome. Each sample sectioned measured 4-6 µm in thickness. The deparaffinized sections were stained with Haematoxylin and Eosin (H&E) stains. The deparaffinized tissue sections were also treated with citrate buffer for antigen retrieval and then incubated with mouse anti-human LLT1 Ab and counter-stained with anti-Mouse-IgG-Dylight 594 Ab. Sections were also stained with the nuclear stain DAPI indicated by the blue stain and imaged on an Olympus AX70 fluorescent microscope and analyzed with Olympus DP70 Image-Pro Plus 5.1 image analysis software. The sections were imaged at 20×, 40× and 100× magnifications.

$^{51}$Cr Release Assay.

DU145, PC3, LNCaP, 22Rv1, PWR-1E, Jurkat, MCF10A, MCF7, MDA-MB-231 and MDA-MB-436 cells were labeled with $^{51}$Cr for 1 hr at 37° C. and then incubated with either 1 µg of unconjugated mouse anti-human LLT1 (0.5 mg/ml) Ab (Lifespan BioSciences, Seattle, Wash.) or mouse IgG1 isotype control Ab (0.5 mg/ml). Primary NK cells isolated from peripheral blood mononuclear cells (PBMC) from a healthy individual were blocked with Fc blocker and then incubated with $^{51}$Cr labeled target cells at Effector to Target (E:T) cell ratios of 25:1, 5:1, and 1:1 for 3.5-4 hours at 37° C. [46]. Supernatants were collected and percent specific lysis was calculated. Experiments were performed in triplicates. Primary NK cells were isolated from PBMC by depletion of non-NK cells through magnetic microbead negative selection NK isolation kit (Miltenyi Biotec, Cologne, Germany) and were cultured in RPMI media supplemented with 15% FBS.

Transfection of Cells with Small Interference RNAs (siR-NAs) and Confirmation of Knockdown by Flow Analysis.

MDA-MB-436 were grown to 80% to 90% confluence on sterile 96-well plates. SMARTpool: ON-TARGETplus CLEC2D (LLT1) 5 nmol small interference RNAs (siRNAs) and ON-TARGETplus non-targeting 5 nmol siRNA 42 (GE Healthcare Dharmacon, Inc., Lafayette, Colo.) were diluted from a 20 µM stock to a 5 µM working stock with 1×siRNA buffer (diluted from 5×siRNA buffer, GE Healthcare Dharmacon, Inc., Lafayette, Colo.). Transfection optimization conditions were determined by GE Healthcare Dharmacon. Manufacturer protocol on transfection was followed (Dharmacon). Cells were transfected with either CLEC2D siRNA or non-targeting siRNA for 63 hours in the 37° C. 5% $CO_2$ incubator. Final concentration of CLEC2D siRNA or non-targeting siRNA was 25 nM. After 63 hours of transfection, confirmation of knockdown of cell surface LLT1 on MDA-MB-436 was confirmed by flow cytometry using anti-human LLT1-PE antibodies or isotype control mouse $IgG_1$-PE antibodies.

REFERENCES

1. American Cancer Society. (2015). Cancer Facts and Figures. pp. 1-70.
2. Bilusic M, Heery C and Madan R A. Immunotherapy in prostate cancer: emerging strategies against a formidable foe. Vaccine. 2011; 29(38):6485-6497.
3. Hanahan D and Weinberg R A. Hallmarks of cancer: the next generation. Cell. 2011; 144(5):646-674.
4. Burotto M, Singh N, Heery C R, Gulley J L and Madan R A. Exploiting synergy: immune-based combinations in the treatment of prostate cancer. Front Oncol. 2014; 4:351.
5. Lanier L L. NK cell recognition. Annual review of immunology. 2005; 23:225-274.
6. Cerwenka A, Lanier, L L. Natural killer cells, viruses, and cancer. Nature Rev Immunol. 2001; 1:41-49.
7. Yokoyama W M, Kim S and French A R. The dynamic life of natural killer cells. Annual review of immunology. 2004; 22:405-429.
8. Vivier E, Nunes J A and Vely F. Natural killer cell signaling pathways. Science. 2004; 306(5701):1517-1519.
9. Bryceson Y T and Long E O. Line of attack: NK cell specificity and integration of signals. Curr Opin Immunol. 2008; 20(3):344-352.
10. Yokoyama W M and Riley J K. NK cells and their receptors. Reprod Biomed Online. 2008; 16(2):173-191.

11. Colonna M. NK cells: new issues and challenges. Preface. Eur J Immunol. 2008; 38(11):2927-2929.
12. Perussia B. Lymphokine-activated killer cells, natural killer cells and cytokines. Curr Opin Immunol. 1991; 3(1):49-55.
13. Rosenberg S A, Dudley M E and Restifo N P. Cancer immunotherapy. N Engl J Med. 2008; 359(10):1072.
14. Rosenberg S A and Dudley M E. Adoptive cell therapy for the treatment of patients with metastatic melanoma. Curr Opin Immunol. 2009; 21(2):233-240.
15. Ben-Efraim S. One hundred years of cancer immunotherapy: a critical appraisal. Tumour Biol. 1999; 20(1):1-24.
BI&action=render&rendertype=fulltext&uid=TBI.tbi20001.
16. Multhoff G, Pfister K, Botzler C, Jordan A, Scholz R, Schmetzer H, Burgstahler R and Hiddemann W. Adoptive transfer of human natural killer cells in mice with severe combined immunodeficiency inhibits growth of Hsp70-expressing tumors. Int J Cancer. 2000; 88(5):791-797.
17. Cooley S, Burns L J, Repka T and Miller J S. Natural killer cell cytotoxicity of breast cancer targets is enhanced by two distinct mechanisms of antibody-dependent cellular cytotoxicity against LFA-3 and HER2/neu. Exp Hematol. 1999; 27(10):1533-1541.
18. Imai K, Matsuyama S, Miyake S, Suga K and Nakachi K. Natural cytotoxic activity of peripheral-blood lymphocytes and cancer incidence: an 11-year follow-up study of a general population. Lancet. 2000; 356(9244):1795-1799.
19. Pasero C, Gravis G, Granjeaud S, Guerin M, Thomassin-Piana J, Rocchi P, Salem N, Walz J, Moretta A and Olive D. Highly effective NK cells are associated with good prognosis in patients with metastatic prostate cancer. Oncotarget. 2015; 6(16):14360-14373.
20. Boles K S, Barten R, Kumaresan P R, Trowsdale J and Mathew P A. Cloning of a new lectin-like receptor expressed on human NK cells. Immunogenetics. 1999; 50(1-2):1-7.
21. Mathew P A, Chuang S S, Vaidya S V, Kumaresan P R, Boles K S and Pham H T. The LLT1 receptor induces IFN-gamma production by human natural killer cells. Mol Immunol. 2004; 40(16):1157-1163.
22. Germain C, Meier A, Jensen T, Knapnougel P, Poupon G, Lazzari A, Neisig A, Hakansson K, Dong T, Wagtmann N, Galsgaard E D, Spee P and Braud V M. Induction of lectin-like transcript 1 (LLT1) protein cell surface expression by pathogens and interferon-gamma contributes to modulate immune responses. J Biol Chem. 2011; 286(44): 37964-37975.
23. Aldemir H, Prod'homme V, Dumaurier M J, Retiere C, Poupon G, Cazareth J, Bihl F and Braud V M. Cutting edge: lectin-like transcript 1 is a ligand for the CD161 receptor. J Immunol. 2005; 175(12):7791-7795.
24. Rosen D B, Bettadapura J, Alsharifi M, Mathew P A, Warren H S and Lanier L L. Cutting edge: lectin-like transcript-1 is a ligand for the inhibitory human NKR-P1A receptor. J Immunol. 2005; 175(12):7796-7799.
25. Germain C, Bihl F, Zahn S, Poupon G, Dumaurier M J, Rampanarivo H H, Padkjaer S B, Spee P and Braud V M. Characterization of alternatively spliced transcript variants of CLEC2D gene. J Biol Chem. 2010; 285(46): 36207-36215.
26. Rosen D B, Cao W, Avery D T, Tangye S G, Liu Y J, Houchins J P and Lanier L L. Functional consequences of interactions between human NKR-P1A and its ligand LLT1 expressed on activated dendritic cells and B cells. J Immunol. 2008; 180(10):6508-6517.
27. Voigt S, Mesci A, Ettinger J, Fine J H, Chen P, Chou W and Carlyle J R. Cytomegalovirus evasion of innate immunity by subversion of the NKR-P1B:Clr-b missing-self axis. Immunity. 2007; 26(5):617-627.
28. Williams K J, Wilson E, Davidson C L, Aguilar O A, Fu L, Carlyle J R and Burshtyn D N. Poxvirus infection-associated downregulation of C-type lectin-related-b prevents NK cell inhibition by NK receptor protein-1B. J Immunol. 2012; 188(10):4980-4991.
29. Bambard N D, Mathew S O and Mathew P A. LLT1-mediated activation of IFN-gamma production in human natural killer cells involves ERK signalling pathway. Scand J Immunol. 2010; 71(3):210-219.
30. Roth P, Mittelbronn M, Wick W, Meyermann R, Tatagiba M and Weller M. Malignant glioma cells counteract antitumor immune responses through expression of lectin-like transcript-1. Cancer Res. 2007; 67(8):3540-3544.
31. Huarte E, Cubillos-Ruiz J R, Nesbeth Y C, Scarlett U K, Martinez D G, Engle X A, Rigby W F, Pioli P A, Guyre P M and Conejo-Garcia J R. PILAR is a novel modulator of human T-cell expansion. Blood. 2008; 112(4):1259-1268.
32. Satkunanathan S, Kumar N, Bajorek M, Purbhoo M A and Culley F J. Respiratory syncytial virus infection, TLR3 ligands, and proinflammatory cytokines induce CD161 ligand LLT1 expression on the respiratory epithelium. J Virol. 2014; 88(5):2366-2373.
33. Chalan P, Bijzet J, Huitema M G, Kroesen B J, Brouwer E and Boots A M. Expression of Lectin-Like Transcript 1, the Ligand for CD161, in Rheumatoid Arthritis. PLoS One. 2015; 10(7):e0132436.
34. Vinay D S, Ryan E P, Pawelec G, Talib W H, Stagg J, Elkord E, Lichtor T, Decker W K, Whelan R L, Kumara H M, Signori E, Honoki K, Georgakilas A G, Amin A, Helferich W G, Boosani C S, et al. Immune evasion in cancer: Mechanistic basis and therapeutic strategies. Semin Cancer Biol. 2015; 35 Suppl:S185-198.
35. Pahl J and Cerwenka A. Tricking the balance: NK cells in anti-cancer immunity. Immunobiology. 2015.
36. Germain C, Guillaudeux T, Galsgaard E D, Hervouet C, Tekaya N, Gallouet A S, Fassy J, Bihl F, Poupon G, Lazzari A, Spee P, Anjuere F, Pangault C, Tarte K, Tas P, Xerri L, et al. Lectin-like transcript 1 is a marker of germinal center-derived B-cell non-Hodgkin's lymphomas dampening natural killer cell functions. Oncoimmunology. 2015; 4(8):e1026503.
37. Lundholm M, Schroder M, Nagaeva O, Baranov V, Widmark A, Mincheva-Nilsson L and Wikstrom P. Prostate tumor-derived exosomes down-regulate NKG2D expression on natural killer cells and CD8+ T cells: mechanism of immune evasion. PLoS One. 2014; 9(9): e108925.
38. Zhang X, Rao A, Sette P, Deibert C, Pomerantz A, Kim W J, Kohanbash G, Chang Y, Park Y, Engh J, Choi J, Chan T, Okada H, Lotze M, Grandi P and Amankulor N. IDH mutant gliomas escape natural killer cell immune surveillance by downregulation of NKG2D ligand expression. Neuro Oncol. 2016.
39. Belting L, Homberg N, Przewoznik M, Brenner C, Riedel T, Flatley A, Polic B, Busch D H, Rocken M and Mocikat R. Critical role of the NKG2D receptor for NK cell-mediated control and immune escape of B-cell lymphoma. Eur J Immunol. 2015; 45(9):2593-2601.
40. Xiao G, Wang X, Sheng J, Lu S, Yu X and Wu J D. Soluble NKG2D ligand promotes MDSC expansion and skews macrophage to the alternatively activated phenotype. J Hematol Oncol. 2015; 8:13.

41. Eisenberger M A, Blumenstein B A, Crawford E D, Miller G, McLeod D G, Loehrer P J, Wilding G, Sears K, Culkin D J, Thompson I M, Jr., Bueschen A J and Lowe B A. Bilateral orchiectomy with or without flutamide for metastatic prostate cancer. N Engl J Med. 1998; 339(15): 1036-1042.
42. Tannock I F, de Wit R, Berry W R, Horti J, Pluzanska A, Chi K N, Oudard S, Theodore C, James N D, Turesson I, Rosenthal M A, Eisenberger M A and Investigators TAX. Docetaxel plus prednisone or mitoxantrone plus prednisone for advanced prostate cancer. N Engl J Med. 2004; 351(15): 1502-1512.
43. Pulukuri S M, Gondi C S, Lakka S S, Jutla A, Estes N, Gujrati M and Rao J S. RNA interference-directed knockdown of urokinase plasminogen activator and urokinase plasminogen activator receptor inhibits prostate cancer cell invasion, survival, and tumorigenicity in vivo. J Biol Chem. 2005; 280(43):36529-36540.
44. Lee J K, Boles K S and Mathew P A. Molecular and functional characterization of a CS1 (CRACC) splice variant expressed in human NK cells that does not contain immunoreceptor tyrosine-based switch motifs. Eur J Immunol. 2004; 34(10):2791-2799.
45. Schneider C A, Rasband W S and Eliceiri K W. NIH Image to ImageJ: 25 years of image analysis. Nat Methods. 2012; 9(7):671-675.
46. Mathew S O, Kumaresan P R, Lee J K, Huynh V T and Mathew P A. Mutational analysis of the human 2B4 (CD244)/CD48 interaction: Lys68 and Glu70 in the V domain of 2B4 are critical for CD48 binding and functional activation of NK cells. J Immunol. 2005; 175(2): 1005-1013.

---

The invention claimed is:

1. A method for treating breast cancer or prostate cancer in a patient in need of such treatment, comprising administering to the patient an antibody or antibody fragment that binds LLT1, the antibody or antibody fragment comprising heavy chain complementarity-determining regions (CDRs) having an amino acid sequence of SEQ ID NO:11, SEQ ID NO:12, and SEQ ID NO:13, and light chain CDRs having an amino acid sequences of SEQ ID NO:15, SEQ ID NO:16, and SEQ ID NO:17, wherein the antibody or antibody fragment binds to cancer cells and inhibits cancer growth or progression.

2. The method of claim 1, wherein the antibody has a heavy chain variable region having an amino acid sequence of SEQ ID NO:10.

3. The method of claim 1, wherein the antibody or antibody fragment thereof is humanized.

4. The method of claim 1, wherein the antibody or antibody fragment thereof is chimeric.

5. The method of claim 1, wherein said antibody or antibody fragment thereof is an antibody fragment, and the antibody fragment is an ScFv.

6. The method of claim 5, wherein the ScFv is murine or humanized.

7. The method of claim 6, wherein the antibody further comprises a heterologous moiety.

8. The method of claim 7, wherein the heterologous moiety is a therapeutic moiety.

9. The method of claim 8, wherein the therapeutic moiety is a cytotoxic moiety.

10. The method of claim 9, wherein the cytotoxic moiety is a cytotoxic agent or radiotoxic agent.

11. The method of claim 10, wherein the cytotoxic moiety is selected from taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, methotrexate, 6-mercaptopurine, 6-thioguanine, cytarabine, fludarabin, 5-fluorouracil decarbazine, mechlorethamine, thioepa chlorambucil, melphalan, carmustine (BSNU), lomustine (CCNU), cyclophosphamide, busulfan, dibromomannitol, streptozotocin, mitomycin C, cis-dichlorodiamine platinum (II) (DDP), daunorubicin, doxorubicin, vincristine, or vinblastine.

12. The method of claim 1, wherein the patient is a human.

13. The method of claim 1, wherein the antibody or antibody fragment thereof is administered parenterally, intraperitoneally, intravenously, subcutaneously, orally, nasally, via inhalation or rectally.

14. The method of claim 1, wherein the antibody or antibody fragment thereof is administered intravenously at a dosage of from 5 mg/m2 to 2000 mg/m2.

15. An anti-LLT1 antibody comprising heavy chain CDRs having an amino acid sequence of SEQ ID NO:11, SEQ ID NO:12, and SEQ ID NO:13, and light chain CDRs having an amino acid sequence of SEQ ID NO:15, SEQ ID NO:16, and SEQ ID NO:17, wherein the antibody binds to cancer cells and inhibits cancer growth or progression.

16. The antibody of claim 15, wherein the antibody is a human antibody.

17. The antibody of claim 15, wherein the antibody has a heavy chain variable region having an amino acid sequence of SEQ ID NO:10.

18. The antibody of claim 15, further comprising a heterologous moiety.

19. The antibody of claim 18, wherein the heterologous moiety is a therapeutic moiety.

20. The antibody of claim 19, wherein the therapeutic moiety is a cytotoxic moiety.

21. The antibody of claim 20, wherein the cytotoxic moiety is a cytotoxic agent or radiotoxic agent.

22. The antibody of claim 20, wherein the cytotoxic moiety is selected from taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, methotrexate, 6-mercaptopurine, 6-thioguanine, cytarabine, fludarabin, 5-fluorouracil decarbazine, mechlorethamine, thioepa chlorambucil, melphalan, carmustine (BSNU), lomustine (CCNU), cyclophosphamide, busulfan, dibromomannitol, streptozotocin, mitomycin C, cis-dichlorodiamine platinum (II) (DDP), daunorubicin, doxorubicin, vincristine, or vinblastine.

\* \* \* \* \*

UNITED STATES PATENT AND TRADEMARK OFFICE
CERTIFICATE OF CORRECTION

PATENT NO. : 11,111,303 B2
APPLICATION NO. : 16/125091
DATED : September 7, 2021
INVENTOR(S) : Mathew et al.

It is certified that error appears in the above-identified patent and that said Letters Patent is hereby corrected as shown below:

On the Title Page

Item (72), the name of Inventor "Purunelloor A. Mathew" should read: --Porunelloor A. Mathew--.

Signed and Sealed this
Tenth Day of May, 2022

Katherine Kelly Vidal
*Director of the United States Patent and Trademark Office*

SEQUENCE LISTING

```
<160> NUMBER OF SEQ ID NOS: 17

<210> SEQ ID NO 1
<211> LENGTH: 191
<212> TYPE: PRT
<213> ORGANISM: Homo sapiens

<400> SEQUENCE: 1

Met His Asp Ser Asn Asn Val Glu Lys Asp Ile Thr Pro Ser Glu Leu
1               5                   10                  15

Pro Ala Asn Pro Gly Cys Leu His Ser Lys Glu His Ser Ile Lys Ala
            20                  25                  30

Thr Leu Ile Trp Arg Leu Phe Phe Leu Ile Met Phe Leu Thr Ile Ile
        35                  40                  45

Val Cys Gly Met Val Ala Ala Leu Ser Ala Ile Arg Ala Asn Cys His
    50                  55                  60

Gln Glu Pro Ser Val Cys Leu Gln Ala Ala Cys Pro Glu Ser Trp Ile
65                  70                  75                  80

Gly Phe Gln Arg Lys Cys Phe Tyr Phe Ser Asp Asp Thr Lys Asn Trp
                85                  90                  95

Thr Ser Ser Gln Arg Phe Cys Asp Ser Gln Asp Ala Asp Leu Ala Gln
            100                 105                 110

Val Glu Ser Phe Gln Glu Leu Asn Phe Leu Leu Arg Tyr Lys Gly Pro
        115                 120                 125

Ser Asp His Trp Ile Gly Leu Ser Arg Glu Gln Gly Gln Pro Trp Lys
    130                 135                 140

Trp Ile Asn Gly Thr Glu Trp Thr Arg Gln Phe Pro Ile Leu Gly Ala
145                 150                 155                 160

Gly Glu Cys Ala Tyr Leu Asn Asp Lys Gly Ala Ser Ser Ala Arg His
                165                 170                 175

Tyr Thr Glu Arg Lys Trp Ile Cys Ser Lys Ser Asp Ile His Val
            180                 185                 190

<210> SEQ ID NO 2
<211> LENGTH: 116
<212> TYPE: PRT
<213> ORGANISM: Artificial Sequence
<220> FEATURE:
<223> OTHER INFORMATION: synthetic peptide

<400> SEQUENCE: 2

Glu Val Gln Leu Gln Gln Ser Gly Ala Asp Leu Val Lys Pro Gly Ala
1               5                   10                  15
```

Ser Val Lys Leu Ser Cys Thr Ala Ser Gly Phe Asn Ile Lys Asp Thr
            20                  25                  30

Tyr Met His Trp Val Ile Gln Arg Pro Glu Gln Gly Leu Asp Trp Ile
        35                  40                  45

Gly Arg Ile Asp Pro Ala Asn Gly Asn Thr Asn Tyr Asp Pro Lys Phe
    50                  55                  60

Arg Ala Lys Ala Thr Ile Thr Ala Asp Thr Ser Ser Asn Thr Ala Tyr
65                  70                  75                  80

Leu Gln Leu Ser Ser Leu Thr Ser Asp Asp Thr Ala Val Tyr Tyr Cys
                85                  90                  95

Ala Gly Met Asp Tyr His Phe Asp Phe Trp Gly Gln Gly Thr Thr Leu
            100                 105                 110

Thr Val Ser Ser
        115

<210> SEQ ID NO 3
<211> LENGTH: 8
<212> TYPE: PRT
<213> ORGANISM: Artificial Sequence
<220> FEATURE:
<223> OTHER INFORMATION: synthetic peptide

<400> SEQUENCE: 3

Gly Phe Asn Ile Lys Asp Thr Tyr
1               5

<210> SEQ ID NO 4
<211> LENGTH: 8
<212> TYPE: PRT
<213> ORGANISM: Artificial Sequence
<220> FEATURE:
<223> OTHER INFORMATION: synthetic peptide

<400> SEQUENCE: 4

Ile Asp Pro Ala Asn Gly Asn Thr
1               5

<210> SEQ ID NO 5
<211> LENGTH: 8
<212> TYPE: PRT
<213> ORGANISM: Artificial Sequence
<220> FEATURE:
<223> OTHER INFORMATION: synthetic peptide

<400> SEQUENCE: 5

Ala Gly Met Asp Tyr His Phe Asp
1               5

<210> SEQ ID NO 6
<211> LENGTH: 108
<212> TYPE: PRT
<213> ORGANISM: Artificial Sequence
<220> FEATURE:
<223> OTHER INFORMATION: synthetic peptide

<400> SEQUENCE: 6

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

```
Lys Tyr Ala Ser Gln Ser Ile Ser Gly Ile Pro Ser Arg Phe Ser Gly
            50                  55                  60

Ser Gly Ser Gly Ser Asp Phe Thr Leu Ser Ile Asn Ser Val Glu Pro
 65                  70                  75                  80

Glu Asp Val Gly Val Phe Tyr Cys Gln Asn Gly His Ser Phe Pro Leu
                 85                  90                  95

Thr Phe Gly Ala Gly Thr Lys Leu Glu Leu Arg Arg
            100                 105
```

<210> SEQ ID NO 7
<211> LENGTH: 6
<212> TYPE: PRT
<213> ORGANISM: Artificial Sequence
<220> FEATURE:
<223> OTHER INFORMATION: synthetic peptide

<400> SEQUENCE: 7

```
Gln Ser Ile Ser Asp Tyr
 1               5
```

<210> SEQ ID NO 8
<211> LENGTH: 3
<212> TYPE: PRT
<213> ORGANISM: Artificial Sequence
<220> FEATURE:
<223> OTHER INFORMATION: synthetic peptide

<400> SEQUENCE: 8

```
Tyr Ala Ser
 1
```

<210> SEQ ID NO 9
<211> LENGTH: 8
<212> TYPE: PRT
<213> ORGANISM: Artificial Sequence
<220> FEATURE:
<223> OTHER INFORMATION: synthetic peptide

<400> SEQUENCE: 9

```
Gln Asn Gly His Ser Phe Pro Leu
 1               5
```

<210> SEQ ID NO 10
<211> LENGTH: 112
<212> TYPE: PRT
<213> ORGANISM: Artificial Sequence
<220> FEATURE:
<223> OTHER INFORMATION: synthetic peptide

<400> SEQUENCE: 10

```
Glu Val Gln Leu Gln Gln Ser Gly Pro Glu Leu Val Lys Pro Gly Ala
 1               5                  10                  15

Ser Val Lys Ile Ser Cys Lys Ala Ser Gly Tyr Ser Phe Thr Gly Asn
             20                  25                  30

Tyr Met His Trp Val Lys Gln Ser Pro Glu Asn Ser Leu Glu Trp Ile
         35                  40                  45

Gly Glu Ile Asn Ile Arg Thr Gly Tyr Ile Ser Tyr Asn Gln Lys Phe
     50                  55                  60

Lys Gly Lys Ala Thr Leu Thr Val Asp Lys Ser Ser Thr Ala Tyr
 65                  70                  75                  80

Met Gln Leu Lys Ser Leu Thr Ser Glu Glu Ser Ala Val Tyr Tyr Cys
                 85                  90                  95
```

```
Thr Arg Ser Ala Tyr Trp Gly Gln Gly Thr Leu Val Thr Val Ser Ala
            100                 105                 110

<210> SEQ ID NO 11
<211> LENGTH: 8
<212> TYPE: PRT
<213> ORGANISM: Artificial Sequence
<220> FEATURE:
<223> OTHER INFORMATION: synthetic peptide

<400> SEQUENCE: 11

Gly Tyr Ser Phe Thr Gly Asn Tyr
1               5

<210> SEQ ID NO 12
<211> LENGTH: 7
<212> TYPE: PRT
<213> ORGANISM: Artificial Sequence
<220> FEATURE:
<223> OTHER INFORMATION: synthetic peptide

<400> SEQUENCE: 12

Ile Asn Ile Arg Thr Gly Tyr
1               5

<210> SEQ ID NO 13
<211> LENGTH: 5
<212> TYPE: PRT
<213> ORGANISM: Artificial Sequence
<220> FEATURE:
<223> OTHER INFORMATION: synthetic peptide

<400> SEQUENCE: 13

Thr Arg Ser Ala Tyr
1               5

<210> SEQ ID NO 14
<211> LENGTH: 108
<212> TYPE: PRT
<213> ORGANISM: Artificial Sequence
<220> FEATURE:
<223> OTHER INFORMATION: synthetic peptide

<400> SEQUENCE: 14

Asp Ile Lys Met Thr Gln Ser Pro Ser Ser Met Tyr Thr Ser Leu Gly
1               5                   10                  15

Glu Arg Val Thr Ile Thr Cys Lys Ala Ser Gln Asp Ile Lys Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Gly Asp Gly Val Pro Ser Arg Val Ser Gly
    50                  55                  60

Ser Gly Ser Gly Gln Asp Tyr Ser Leu Thr Ile Gly Ser Leu Glu Tyr
65                  70                  75                  80

Glu Asp Met Gly Ile Tyr Tyr Cys Leu Gln Tyr Ala Glu Phe Pro Arg
                85                  90                  95

Thr Phe Gly Gly Gly Thr Lys Leu Glu Ile Arg Arg
            100                 105

<210> SEQ ID NO 15
<211> LENGTH: 6
<212> TYPE: PRT
<213> ORGANISM: Artificial Sequence
```

```
-continued

<220> FEATURE:
<223> OTHER INFORMATION: synthetic peptide

<400> SEQUENCE: 15

Gln Asp Ile Lys Ser Tyr
1               5

<210> SEQ ID NO 16
<211> LENGTH: 3
<212> TYPE: PRT
<213> ORGANISM: Artificial Sequence
<220> FEATURE:
<223> OTHER INFORMATION: synthetic peptide

<400> SEQUENCE: 16

Arg Ala Asn
1

<210> SEQ ID NO 17
<211> LENGTH: 9
<212> TYPE: PRT
<213> ORGANISM: Artificial Sequence
<220> FEATURE:
<223> OTHER INFORMATION: synthetic peptide

<400> SEQUENCE: 17

Leu Gln Tyr Ala Glu Phe Pro Arg Thr
1               5
```